(12) United States Patent
DeRuntz et al.

(10) Patent No.: US 7,291,132 B2
(45) Date of Patent: Nov. 6, 2007

(54) MEDICATION DISPENSING APPARATUS WITH TRIPLE SCREW THREADS FOR MECHANICAL ADVANTAGE

(75) Inventors: Otto Daniel DeRuntz, Dunstable, MA (US); Kenneth Allen Focht, Needham, MA (US); Alexander Thomas Jacobs, Somerville, MA (US); Elizabeth Whitney Johansen, Allston, MA (US); Jared Alden Judson, Topsfield, MA (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/567,196

(22) PCT Filed: Aug. 9, 2004

(86) PCT No.: PCT/US2004/022312

§ 371 (c)(1),
(2), (4) Date: Feb. 3, 2006

(87) PCT Pub. No.: WO2005/018721

PCT Pub. Date: Mar. 3, 2005

(65) Prior Publication Data

US 2006/0206057 A1    Sep. 14, 2006

(51) Int. Cl.
*A61M 5/00* (2006.01)
(52) U.S. Cl. .................. 604/207; 604/211; 604/187
(58) Field of Classification Search .................. 604/187
See application file for complete search history.

(56) References Cited

U.S. PATENT DOCUMENTS

| | | | |
|---|---|---|---|
| 4,470,317 A | 9/1984 | Sabloewski et al. | |
| 4,498,904 A | 2/1985 | Turner et al. | |
| 4,585,439 A | 4/1986 | Michel | |
| 4,883,472 A | 11/1989 | Michel | |
| 4,973,318 A | 11/1990 | Holm et al. | |

(Continued)

FOREIGN PATENT DOCUMENTS

DE    3609555    9/1987

(Continued)

OTHER PUBLICATIONS

Eli Lilly and Company, Technical Dossier for the HumaPen® Pen-Injector Family, Aug. 15, 2000, pp. 1 and 10-25 provided.

*Primary Examiner*—Nicholas D. Lucchesi
*Assistant Examiner*—Laura A. Bouchelle
(74) *Attorney, Agent, or Firm*—Edward J. Prein

(57) ABSTRACT

A medication dispensing apparatus that provides a mechanical advantage. During dose preparing, a nut rotating element (410) and a screw element (368) are in a first axial arrangement such that a screwing motion of the nut rotating element and screw element relative to the apparatus housing that moves the elements a first axial distance from a home position screws a nut (364) along a drive member threaded shaft (362) a second axial distance different than the first axial distance. During dose dispensing, the nut rotating element and the screw element are in a second axial arrangement, whereby a screwing motion of the screw element relative to the housing back toward the home position advances a plunger (366) in the distal direction to axially advance the nut and thereby the drive member and a fluid container piston to dispense medicine.

22 Claims, 24 Drawing Sheets

U.S. PATENT DOCUMENTS

| | | | |
|---|---|---|---|
| 5,112,317 A | | 5/1992 | Michel |
| 5,279,585 A | * | 1/1994 | Balkwill ............... 604/207 |
| 5,304,152 A | | 4/1994 | Sams |
| 5,320,609 A | | 6/1994 | Haber et al. |
| 5,626,566 A | | 5/1997 | Petersen et al. |
| 5,674,204 A | | 10/1997 | Chanoch |
| 5,688,251 A | | 11/1997 | Chanoch |
| 5,743,889 A | | 4/1998 | Sams |
| 5,800,388 A | | 9/1998 | Schiff et al. |
| 5,820,602 A | | 10/1998 | Kovelman et al. |
| 5,938,642 A | | 8/1999 | Barroughs et al. |
| 6,003,736 A | | 12/1999 | Ljunggren |
| 6,004,297 A | | 12/1999 | Steenfeldt-Jensen et al. |
| 6,074,372 A | | 6/2000 | Hansen |
| 6,086,567 A | | 7/2000 | Kirchhofer et al. |
| 6,096,010 A | | 8/2000 | Walters et al. |
| 6,221,046 B1 | | 4/2001 | Burroughs et al. |
| 6,221,053 B1 | | 4/2001 | Walters et al. |
| 6,235,004 B1 | | 5/2001 | Steenfeldt-Jensen et al. |
| 6,277,099 B1 | * | 8/2001 | Strowe et al. ............ 604/207 |
| 6,383,167 B2 | | 5/2002 | Kirchhofer et al. |
| 6,663,602 B2 | | 12/2003 | Moller |
| 7,094,221 B2 | | 8/2006 | Veasey et al. |
| 2002/0029018 A1 | | 3/2002 | Jeffrey |
| 2004/0059299 A1 | | 3/2004 | Moller |
| 2005/0209570 A1 | | 9/2005 | Moller |
| 2006/0258988 A1 | | 11/2006 | Keitel et al. |

FOREIGN PATENT DOCUMENTS

| | | |
|---|---|---|
| EP | 0 897 728 A1 | 2/1999 |
| EP | 1 095 668 A1 | 5/2001 |
| EP | 1 610 848 B1 | 1/2006 |
| WO | WO96/26754 | 9/1996 |
| WO | WO98/57688 | 12/1998 |
| WO | WO 00/41754 | 7/2000 |
| WO | WO 01/10484 A1 | 2/2001 |
| WO | WO 01/95959 A1 | 12/2001 |
| WO | WO 03/008023 A1 | 1/2003 |
| WO | WO 03/086512 A1 | 10/2003 |
| WO | WO 2004/030730 A2 | 4/2004 |
| WO | WO 2004/078239 A1 | 9/2004 |
| WO | WO 2004/078240 A2 | 9/2004 |
| WO | WO 2004/089450 A1 | 10/2004 |

* cited by examiner

MEDICATION DISPENSING APPARATUS WITH TRIPLE SCREW THREADS FOR MECHANICAL ADVANTAGE

BACKGROUND OF THE INVENTION

The present invention pertains to medication dispensing devices, and, in particular, to a portable medication dispensing device such as an injector pen.

Patients suffering from a number of different diseases frequently must inject themselves with medication. To allow a person to conveniently and accurately self-administer medicine, a variety of devices broadly known as injector pens or injection pens have been developed. Generally, these pens are equipped with a cartridge including a piston and containing a multi-dose quantity of liquid medication. A drive member, extending from within a base of the injector pen and operably connected with typically more rearward mechanisms of the pen that control drive member motion, is movable forward to advance the piston in the cartridge in such a manner to dispense the contained medication from an outlet at the opposite cartridge end, typically through a needle that penetrates a stopper at that opposite end. In disposable or prefilled pens, after a pen has been utilized to exhaust the supply of medication within the cartridge, a user, who then begins using a new replacement pen, discards the entire pen. In reusable pens, after a pen has been utilized to exhaust the supply of medication within the cartridge, the pen is disassembled to allow replacement of the spent cartridge with a fresh cartridge, and then the pen is reassembled for its subsequent use.

A number of known injection pens have utilized a mechanical advantage to facilitate operation. An injection pen disclosed in International Publication Number WO 96/26754 obtains a mechanical advantage with a gear set including first and second coaxial pinions that engage different racks within the pen, and which gear set travels with the pen thrust rod. Another injection pen with a mechanical advantage is disclosed in International Publication Number WO 01/95959, which pen uses one or more gear wheels carried by a connector element threadedly engaged with a piston rod. While these pens may be useful, their ability to provide high mechanical advantage may be limited by, for example, how small the gears can be made. In addition, these pens have relatively complicated designs, as well as potentially costly components, such as separate springs, which may undesirably impact the ability to effectively commercialize the pen in a disposable format.

Some other known injection pens that provide mechanical advantage have complicated designs that may make them relatively expensive to produce. Still another injection pen, such as disclosed in U.S. Pat. No. 5,938,642, is highly effective as a pre-filled device, but does not provide a mechanical advantage during injecting.

Thus, it would be desirable to provide an apparatus that can overcome one or more of these and other shortcomings of the prior art.

BRIEF SUMMARY OF THE INVENTION

In one form thereof, the present invention provides a medication dispensing apparatus including a housing, a drive member rotatably fixed during dose preparing and injecting and axially movable in a distal direction relative to the housing, which drive member includes a threaded shaft, a fluid container defining a medicine-filled reservoir with a movable piston at one end and an outlet at the other end, which piston is engagable by the drive member to be advanced toward the outlet when the drive member is moved distally, a nut screwable along the drive member threaded shaft, a screw element threadedly engaged with the housing to be screwable relative to the housing, a nut rotating element connected with the nut to be axially movable and rotatably fixed relative thereto, which nut rotating element is rotatably fixed with the screw element when the nut rotating element and the screw element are in a first axial arrangement, which nut rotating element is rotatable relative to the screw element when the nut rotating element and the screw element are in a second axial arrangement, and a nut advancing plunger threadedly engaged with the screw element, which plunger is axially movable and rotatably fixed relative to the housing. During dose preparing, the nut rotating element and the screw element are in the first axial arrangement, whereby a screwing motion of the nut rotating element and screw element relative to the housing screws the nut rotating element and the screw element a first axial distance from a home position, which screwing motion of the nut rotating element screws the nut along the drive member threaded shaft a second axial distance different than the first axial distance. During dose dispensing, the nut rotating element and the screw element are in the second axial arrangement, whereby a screwing motion of the screw element relative to the housing back toward the home position advances the plunger in the distal direction to axially advance the nut and thereby the drive member and the fluid container piston to dispense medicine from the outlet.

One advantage of the present invention is that a medication dispensing apparatus can be provided with a mechanical advantage that makes easier the plunging needed to dispense medication, which mechanical advantage can be very high and conveniently selected by the manufacturer during apparatus design.

Another advantage of the present invention is that a medication dispensing apparatus can be provided with an externally accessible plunging member that when plunged travels a greater distance than the cartridge piston engaging drive member it advances, whereby even smaller doses achieved with shorter drive member movements can involve meaningful plunging member motion.

Still another advantage of the present invention is that a medication dispensing apparatus can be provided which is mechanically efficient, and the high level of this efficiency may allow suitable operating characteristics of the apparatus to be achieved even with less expensive component parts.

Still another advantage of the present invention is that a medication dispensing apparatus can be provided which can be made from a number of parts and at a cost which makes it justifiably disposable after its medication contents are exhausted.

Yet another advantage of the present invention is that a medication dispensing apparatus can be provided with a compact design that contributes to a short axial length and a small diameter of the apparatus.

Yet another advantage of the present invention is that a medication dispensing apparatus can be provided which achieves a rotate to set a variable, desired dose, push to inject dose functionality with a limited amount of parts and complexity.

Yet another advantage of the present invention is that a medication dispensing apparatus can be provided which may be relatively low cost due to the use of compliant plastic to achieve functionality rather than metal springs.

Yet another advantage of the present invention is that a medication dispensing apparatus can be provided with a high mechanical advantage that does not require any small gears having a performance that may be uncertain due to, for example, the possibility of the teeth of the gears failing during operation if injection molded from an inexpensive plastic.

Another advantage of the present invention is that a medication dispensing apparatus can be provided with an integral insufficient remaining dose indicator that does not impact the force required to inject or set a dose.

Still another advantage of the present invention is that a medication dispensing apparatus can be provided that does not require a dedicated anti-back drive feature, or an injection clicker, and as a result the apparatus can be less complicated in design.

BRIEF DESCRIPTION OF THE DRAWINGS

The above-mentioned and other advantages and objects of this invention, and the manner of attaining them, will become more apparent, and the invention itself will be better understood by reference to the following description of embodiments of the invention taking in conjunction with the accompanying drawings, wherein.

Figure 1:
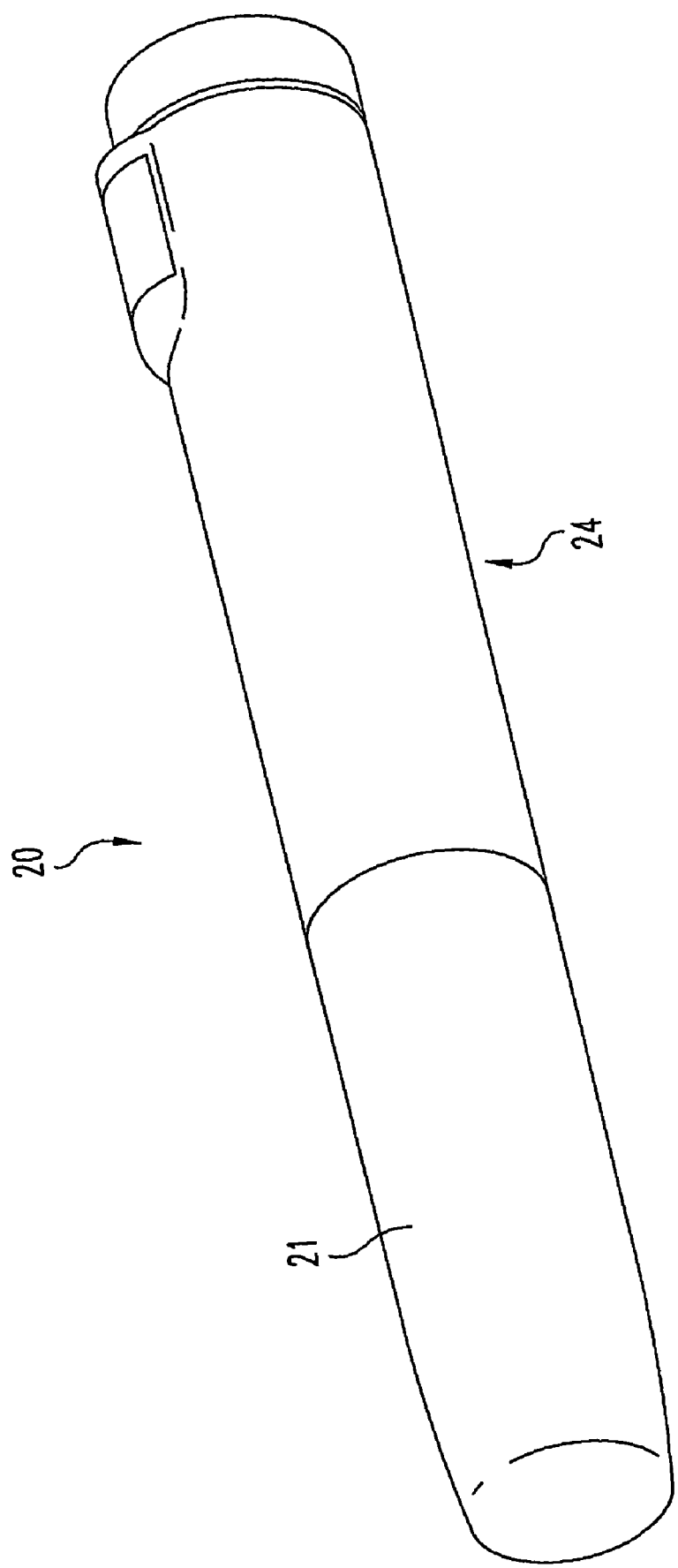
FIG. 1 is a front perspective view of a first embodiment of a medication dispensing apparatus with mechanical advantage of the present invention, which apparatus is capped as well as arranged in a ready or zero dose state.

Corresponding reference characters indicate corresponding parts throughout the several views. Although the drawings represent embodiments of the present invention, the drawings are not necessarily to scale, and certain features may be exaggerated or omitted in some of the drawings in order to better illustrate and explain the present invention.

DETAILED DESCRIPTION OF THE INVENTION

Figure 2:
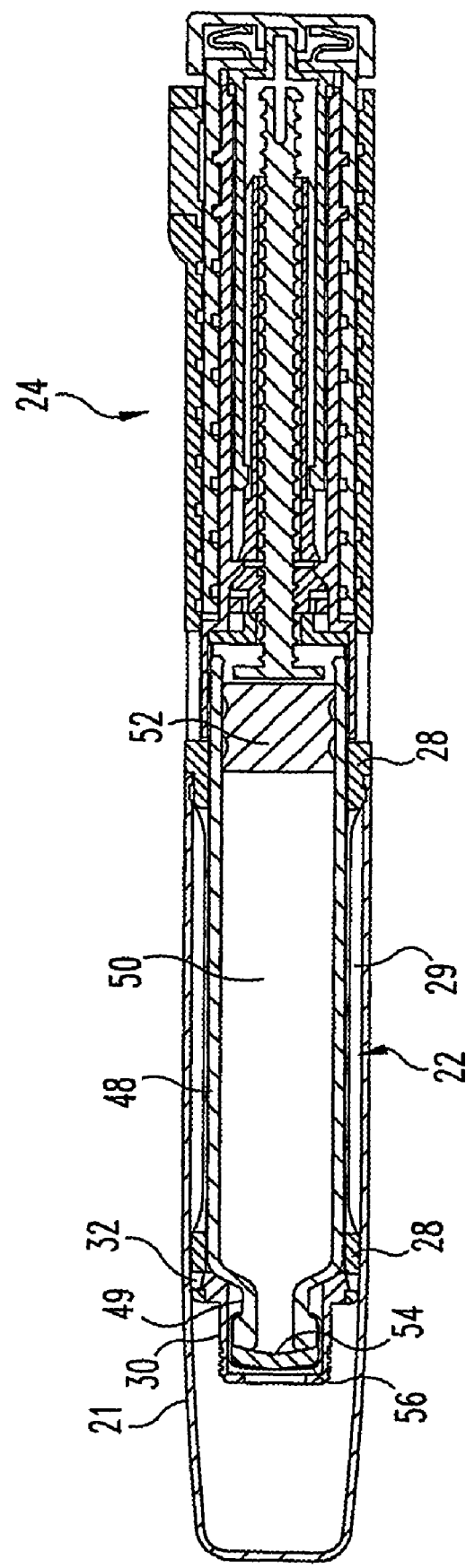
FIG. 2 is a front view in longitudinal cross-section of the medication dispensing apparatus of FIG. 1.
Figure 3:
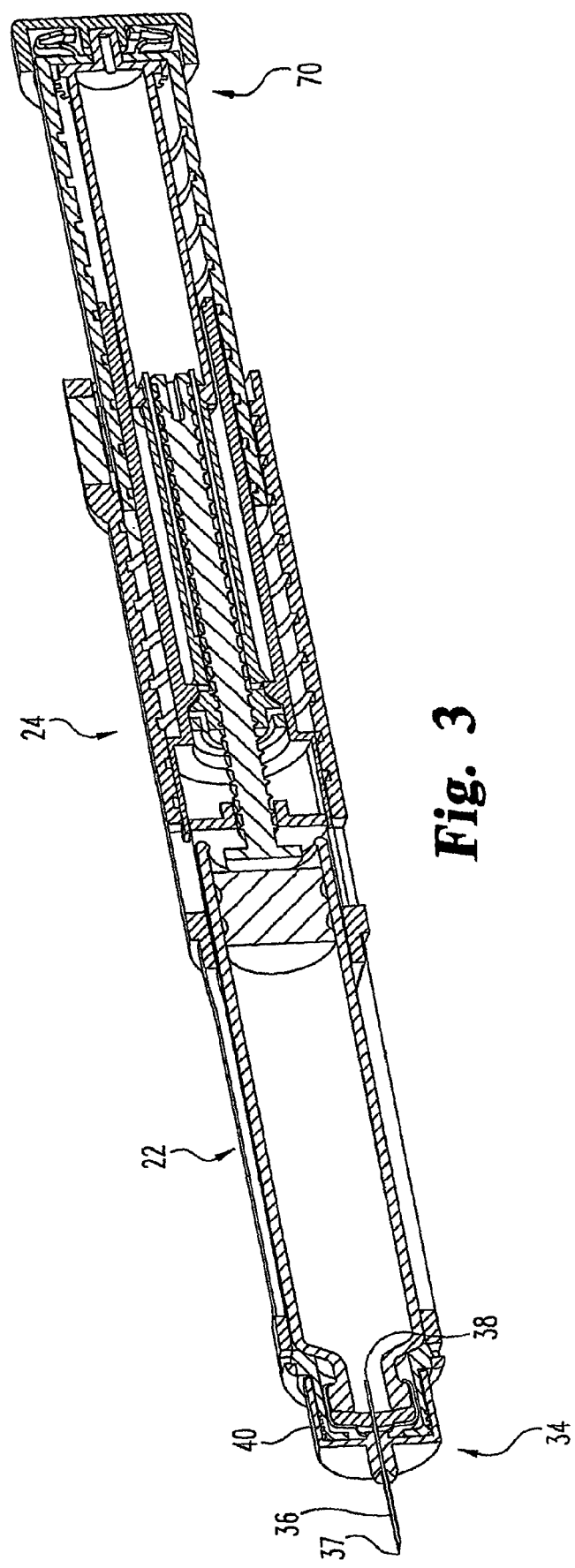
FIG. 3 is a front perspective view in longitudinal cross-section of the medication dispensing apparatus of FIG. 1, but with the apparatus cap removed, with a needle assembly attached, and after the apparatus has been manipulated from its ready state to a ready-to-inject state.

Referring now to FIGS. 1-3, there is shown a first embodiment of a medication dispensing apparatus of the present invention. Any directional references in this detailed description with respect to FIG. 1 or any of the other Figures, such as right or left, upper or lower, or clockwise or counterclockwise, are intended for convenience of description, and by itself does not limit the present invention or any of its components to any particular positional or spatial orientation.

The apparatus, generally designated 20, is shown as an injector pen, which pen has an elongated, substantially writing instrument-like form, although other forms are within the scope of the invention. Medication injector pen 20 is a disposable or prefilled pen, in that after the quantity of medicine contained therein is exhausted by multiple operations of the pen, the entire pen is discarded rather than being reset and reloaded with a replacement container of medicine. Pen 20 is operable by a user to select and then inject any one of a number of different size doses, such as may be appropriate with some therapeutics loaded therein by the manufacturer, for example insulin. Pen 20 can also be adapted to deliver a dose in a specific amount appropriate for some other types of therapeutics loaded therein by the manufacturer.

Injector pen 20 generally includes a distal portion 22 and a proximal portion 24. Distal portion 22 contains the medicinal fluid to be outlet at its distal end upon pen operation, and this portion is shown received within pen cap 21 in FIGS. 1 and 2. The outlet end of distal portion 22 is equipped in FIG. 3 with an injection needle. Proximal portion 24 contains the injecting mechanism used to force the contained medicine from the needled end.

Distal portion 22 includes a retainer with a cartridge 48 held therein. The cartridge retainer is shown formed in majority part as a distal extension 28 of the injection mechanism housing of pen 20, which is made of an opaque plastic. Windows 29 in extension 28 allow the contents of the cartridge to be seen to let a user estimate the medicine remaining. The retainer is formed in additional part as a stepped-down, injection molded plastic cap 30 that has a plurality of tabs 32, such as two, three or four tabs on the outer periphery that snap lock during manufacture into complementary apertures in extension 28. Other means of connecting the cap to the retainer extension may alternatively be employed, such as adhesives or ultrasonic welding. Suitable connection means, such as external threads, are provided on cap 30 to releasably connect a pen-needle assembly, generally designated 34. Not shown crush ribs may be molded into the interior of the retainer to hold cartridge 48 axially fixed between such crush ribs and an inner surface of the cap 30.

Pen-needle assembly 34 is of known design and includes a double-ended needle cannula or injection needle 36 having a distal tip 37 at one end and a proximal point 38 at the other. Injection needle 36 is mounted in a tubular hub 40 that is structured, such as via internal threading, to cooperate with the shown retainer design so as to be removably mounted to the retainer distal end. A not shown needle cap mounted to the hub, which needle cap is removed when pen 20 is used to inject medicine, may protect tip 37. Although the needle assembly is shown as having a single injection needle, needle assemblies which may be used with pen 20 may be of various types known in the art, including, but not limited to, assemblies with one or more shortened injection needles, including microneedle arrays.

Cartridge 48 is of conventional design and defines a medicine-filled reservoir 50 that is closed at its proximal end by a piston 52 that is axially slidably and sealably engaged with the cartridge interior wall to hold the fluid medication within reservoir 50. The distal, outlet end of cartridge reservoir 50 is sealed by a septum 54 held by a cap 56 that is secured to a stepped-down diameter neck portion 49 of the cartridge. When pen-needle assembly 34 is mounted on cap 30, the proximal point 38 of injection needle 36 passes through a central opening in the distal end of cap 30, an opening in cap 56, and penetrates cartridge septum 54 to provide a fluid flow outlet by which medicine within cartridge reservoir 50 can be dispensed from needle tip 37 during operations of injector pen 20.

The fluid medicine container shown and described above is illustrative and not intended to be limiting as other constructions may be employed within the scope of the invention. For example, rather than the shown container in which a distinct cartridge is held by a cap within a retainer portion integrally formed with the rest of the pen housing, in another fluid container embodiment, the cartridge could be constructed to be sufficiently durable and adapted to secure directly to a pen proximal portion 24 without any protective retainer there around, and with the pen-needle assembly directly mountable to the cartridge. Still further, and similar to other known pens as well as pen 320 of FIGS. 22-26, the proximal extension of the housing and the cap 30 shown in pen 20 can be eliminated and the cartridge could be slidably inserted and held in a one-piece retainer that extends the cartridge length, that removably mounts a pen needle assembly at its distal end, and that has a proximal end. In the case of a disposable pen, such proximal end can be fixedly mounted or secured, via adhesives, ultrasonic welding or in another suitable manner, to the injecting mechanism housing of an assembled pen portion when its injector pen is assembled by the manufacturer, while in the case of a reusable pen, wherein the retainer may be reusable, such proximal end can be removably mounted or secured, such as via a threaded connection, to a reusable injecting mechanism pen portion having a resettable drive member. In this one-piece retainer design, the cartridge may be axially constrained directly between the retainer interior surface and a portion of, for example, the housing without the use of crush ribs.

Figure 4:
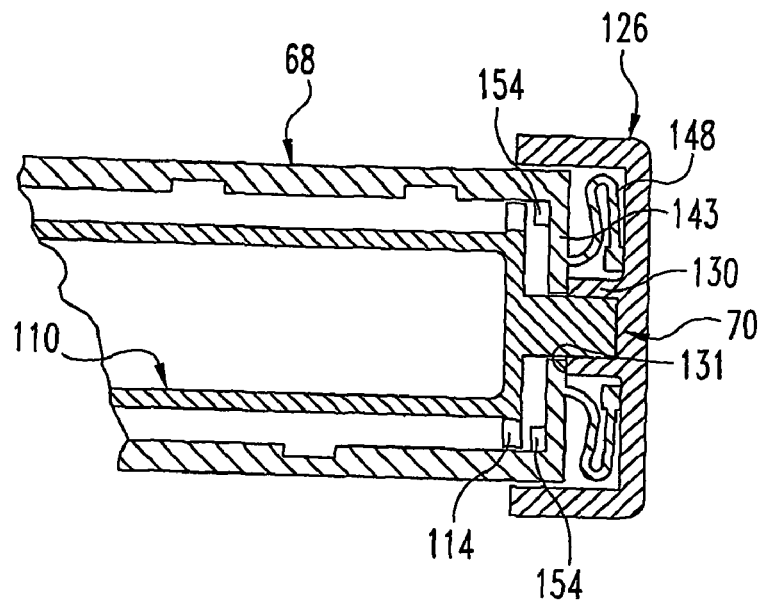
FIG. 4 is an enlarged view of select portions of the apparatus of FIG. 3 during the initial actuator plunging associated with injecting.
Figure 5:
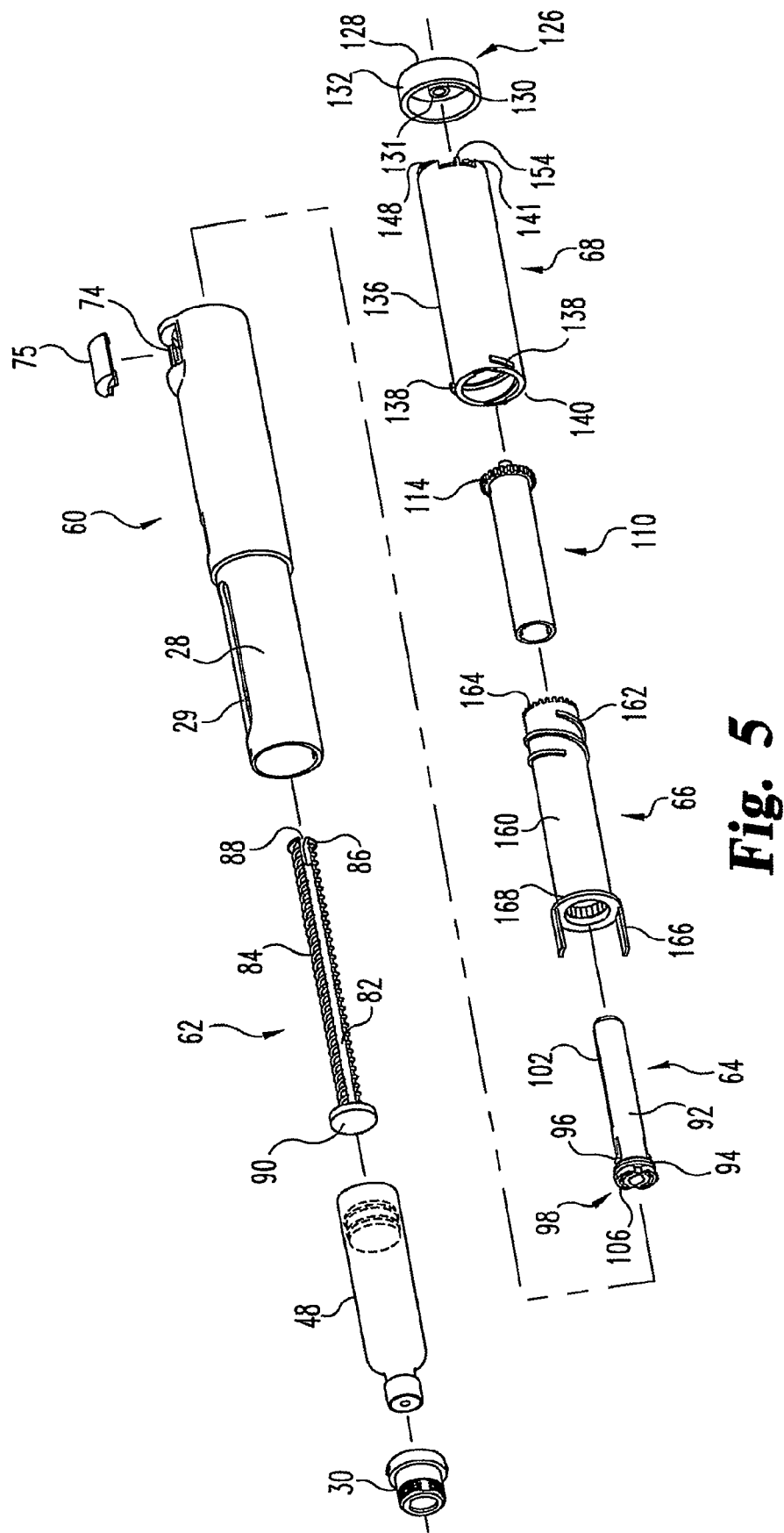
FIG. 5 is an exploded, perspective view of portions of the apparatus of FIG. 2.
Figure 6:
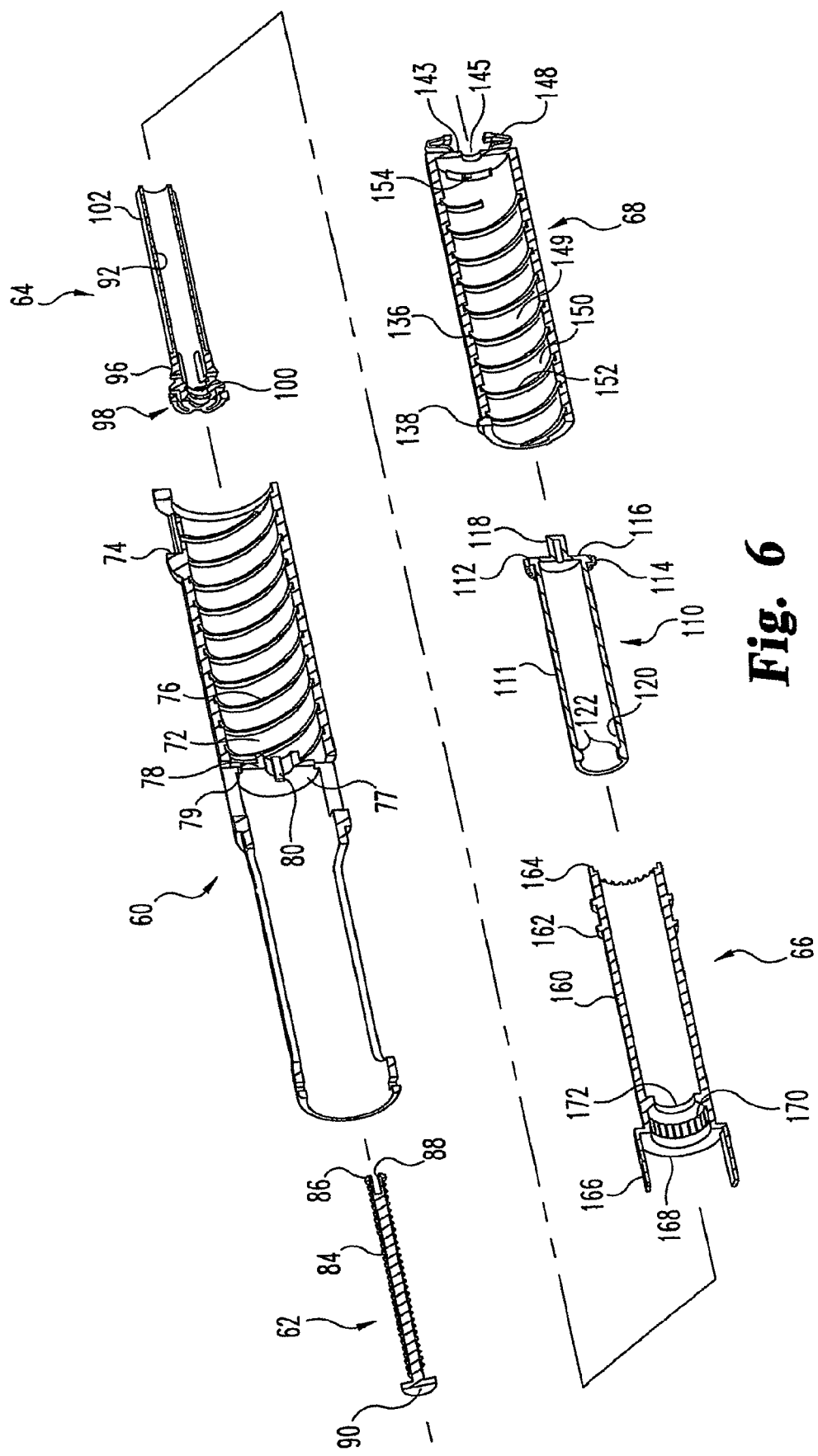
FIG. 6 is a longitudinal cross-sectional view of portions of FIG. 5.

With additional reference to FIGS. 4-6, pen proximal portion 24 of injector pen 20 includes an external, protective housing 60, an axially advanceable drive member 62, a nut 64, a nut advancing plunger 66, a screw element 68, and an actuator 70 that is used to set the dose and then inject the set dose.

Housing 60 is formed from a lightweight material, such as injection molded plastic. The housing may be molded as a single, tubular piece for robustness. The tubular body of housing 60 defines an internal hollow 72 in which drive member 62 extends in an axial or longitudinal direction. A window 74 in the housing near its proximal end is shown filled with a magnifying lens 75 that snaps fits to the housing. Lens 75 is optional in other embodiments and allows dosage indicating markings on a dial to be readily visible during use. The exterior of housing 60 is formed with one or more elements, such as detents, formed cooperatively with the pen cap configuration to allow a removable snap-mounting of pen cap 21 to housing 60.

Near the distal end of proximal portion 24, housing 60 is formed with an inner annular shoulder 77. A central opening of shoulder 77 is ringed by a proximally extending collar 78 that provides support for drive member 62. At least one drive member anti-rotation element extends radially inward from collar 78 into hollow 72 and projects distally of the collar 78. The shown anti-rotation element is provided in the form of a pair of diametrically opposed elements or tabs 80 having squared off inward ends that each slidably fit within longitudinal keyways 82 in drive member 62. In alternate embodiments, features other than tabs and keyways, for instance a drive member with flats that fits within a complementarily shaped hole in the collar, may be used to prevent rotation. Tabs 80 prevent drive member 62 from rotating within housing 60 during pen use, but permit drive member 62 to be shifted longitudinally, such as in the distal direction toward the cartridge. Although tabs 80 and shoulder 77 are shown integrally formed and therefore rotatably fixed with housing 60, a shoulder with tabs may be separately formed and then assembled to the housing to be rotatably fixed relative thereto. Such assembly for pen 20, which may be accomplished with a snap fit connection of the shoulder to the tubular housing that prevents axial and rotational relative motion, may also be accomplished with a shoulder and housing design that alone results in a rotational fixing but not a complete axial fixing of the shoulder and housing, with the axial positioning and securement of the shoulder being a result of it being pressed into place against a feature of the housing by the cartridge during pen assembly. In addition, if it is desired to provide the drive member with an anti-backup element, tabs 80 could include teeth that engage an optional rack within the slots of the drive member, or the tabs could be constructed to grip into the plastic of the drive member, to prevent the drive member from being moved within the housing in the proximal direction during use, but which do not prevent the drive member from being advanced in the distal direction toward cartridge 48.

Drive member 62 is in the form of a screw that is axially translatable and rotatably fixed during dosing and injecting. Drive member 62 includes a shaft with a helical threading 84 along its length, which threading is interrupted by longitudinally extending keyways or grooves 82. A thread stop 86 shown at the proximal end of threading 84 is provided and is used in preventing the pen from being set by a user to deliver a dose of medicine larger than remains in cartridge 48. Thread stop 86 is shown disposed on flanges of the screw defined at the proximal screw end by a diametric relief notch 88, which notch allows the thread stop to be cammed in and pass by the nut thread during pen assembly, but which thread stop, after passing the nut threads during assembly, then resiliently returns to a functional position. Other forms of stopping the screw motion may be substituted within the scope of the invention. For example, in an embodiment where the shaft and foot are separately formed and then assembled during pen assembly, the notch at the proximal screw end can be eliminated, and the threading at the proximal screw end could stop near the proximal end where it can not be cammed in, and such solid screw with thread stop better ensures the nut will not be torqued off the screw during dose preparing.

The distal end of drive screw 62 includes an enlarged, disc-shaped foot 90 to distribute loading on the cartridge piston 52 that the foot contacts and thereby directly engages during piston advancing. Drive screw 62 is shown as being a one-piece plastic injection molding. Other constructions of the drive member, including as an assembly of separately formed component parts as alluded to above, is within the scope of the invention. For example, if, unlike in the assembly sequence described below, the threaded shaft is intended to be moved distally through the nut during assembly, such as to allow for a more robust thread stop described above, or to allow the screw to include an anti-backup rack described above, the separate foot can be attached, such as with a snap fit that may permit relative rotation, to the threaded shaft end previously passed through the nut.

Figure 7:
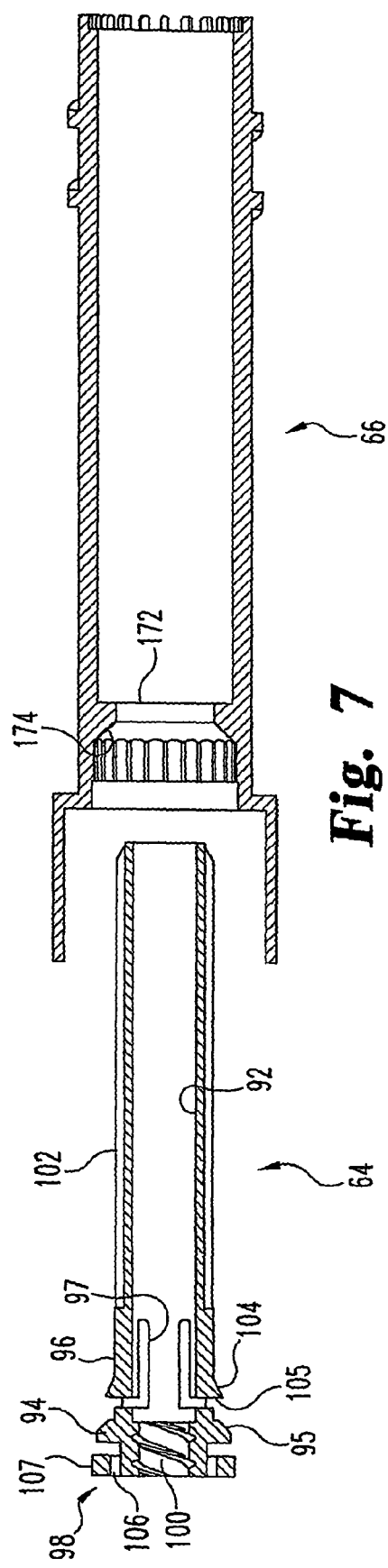
FIGS. 7-18 are longitudinal cross-sectional views of an assembly sequence of the medication dispensing apparatus of FIG. 1.

Nut 64 includes a cylindrical, tube-shaped body 92, plunging rib 94, flexible assembly fingers 96 and clicker members 98. The distal region of body 92 is formed with an internal threading 100 that threadedly engages in a friction locking fashion the drive screw threading 84. Threadings 100 and 84 are shown as a double start threading but may be differently formed while still providing suitable friction locking capabilities, such as a single start threading or another multiple start threading. For a single start threading, threading 100 may extend slightly less than a single turn, and therefore slightly less than 360°, to facilitate molding by allowing use of axial core pins instead of an unscrewing core pin in the molding process. Rib 94 radially protrudes from and extends circumferentially around body 92. Referring additionally to FIG. 7, rib 94 includes a sloped proximal face 95 adapted for engagement, such as a direct engagement via abutting contact, with plunger 66 during injecting. The hollow interior of nut body 92 proximal of threading 100 allows free passage of the proximal end of drive screw 62.

The exterior surface of nut body 92 is cooperatively designed with actuator 70 so that the actuator is axially free and rotatably fixed relative thereto. Thus, during use the actuator is axially moveable relative to, but rotatably locked with, the threaded nut. This connection is shown obtained using at least one, such as at least two, angularly spaced slots or grooves 102 in the exterior surface of nut body 92 proximally of rib 94. Grooves 102 extend longitudinally and slidably accommodate keys 122 of nut-engaging sleeve 110.

Assembly fingers 96 serve to prevent nut 64 from coming off plunger 66 after being assembled thereto during manufacture. The length of assembly fingers 96 is defined by U-shaped openings 97 through body 92. The radially protruding tips of fingers 96 each includes a ramp-shaped proximal face 104, and a distal face 105 aligned perpendicular to the axis of the nut body.

Clicker members 98 cooperate with complimentary elements provided on the drive sleeve to provide a clicker function during dose setting. The nut clicker members are shown including at least one, such as two, flexible convex webs 106 that bow outward from nut body 92. Each web 106 includes a bi-directional tooth 107 at the center of its length that snaps over, in either direction of rotation, a ring of bi-directional, longitudinal ribs 170 formed in drive sleeve 66. Ribs 70 define detents at each of the plurality of angular positions corresponding to increments in dose volume. As few as one clicker element may be provided, but the use of two equally angularly spaced teeth as shown, or more teeth, such as four teeth, equally angularly spaced aids in centering nut 64 within the plunger or drive sleeve designated 66. Nut 64 is shown as being a one-piece plastic injection molding, but other constructions are within the scope of the invention.

In the first embodiment, and with primary reference to FIGS. 5 and 6, actuator 70 includes a tubular, cylindrical nut-engaging sleeve 110 formed in one piece of an injection molded plastic and which fits within housing hollow 72. A flange 112 that rings the proximal end of the body 111 of sleeve 110 includes radially extending, square shaped teeth 114. The proximal end of body 111 has a closed face 116, and stem 118 axially extends from the center of face 116 in the proximal direction. Adjacent its distal end, the interior surface 120 of body 111 includes a pair of diametrically arranged ribs or keys 122 that are slidably received in the straight keyways 102 formed in nut 64. Although shown as being finite in length, keys that extend the entire longitudinal length of nut-engaging sleeve 110 may facilitate molding.

Actuator 70 also includes a button 126 extending proximally of housing 60 in the zero dose pen arrangement. Button 126 is injection molded from plastic with a disk shaped proximal face 128 and a mounting collar 130 centrally located on a distal surface. Button face 128 serves as a push surface against which a force can be applied manually (i.e. directly by user contact) to push the actuator to the left from the perspective of a viewer of FIG. 3. Collar 130 is secured to stem 118, such as with a keyed fit and an ultrasonic weld, so as to axially and rotatably fix together button 126 and nut-engaging sleeve 110. Button 126 further includes a depending lip or flange 132 that distally extends from the radial periphery of the button distal face. Lip 132, which serve as a grip portion that is externally accessible to be manually rotated by a user for dose setting purposes, may be knurled or otherwise formed to facilitate being gripped by a user's fingers.

Coaxially mounted around nut-engaging sleeve 110 is a screw element 68. Screw element 68 serves as the dial in the first embodiment due to dose indicating markings (not shown) provided on its exterior. Screw element 68 is formed in one piece of an injection molded plastic and includes a cylindrical exterior surface 136 having a threading 138 along a portion of its axial length between the distal end 140 and the proximal end 141. Threading 138 is shown formed by angularly spaced thread sections properly oriented in a helical arrangement, and engages a corresponding threading 76 formed on the interior surface of housing 60 to threadedly engage the screw element to the pen housing. Threadings 138 and 76 are shown as a triple start threading but may be differently formed, such as a single start threading or another multiple start threading. For such triple start threading, the shown thread sections of 138 correspond to the three thread starts. Exterior surface 136 is sized to freely insert within button 126 such that depending lip 132 is disposed radially outward of and axially extends distally of proximal end 141. Proximal end 141 has an annular face 143 that defines a central opening 145 through which fits nut-engaging sleeve stem 118. To serve as a dose-indicating dial, screw element 68 includes around its exterior surface 136 suitable indicia of therapeutic dose size as visible through lens 75. When pen 20 is to be used for insulin in which the dose delivered is desired to be any of a variety selectable by a user, the indicia is provided in the form of a helically arranged pattern of numerals, such as from zero to the maximum allowed by the pen, such as 60 or 80, in two unit increments, with odd dose sizes being represented by hash marks between the even numbered dose sizes. Different indicia can be used for different pens, such as if the pen were intended to deliver a fixed dose.

Disposed between screw element 68 and actuator 70 are biasing means used to urge the components away from each other in an axial direction. The biasing means are shown provided in the form of one or more resilient leaf springs or flexures 148 formed, for example, integrally with dial 68. In alternate embodiments, different biasing means, such as metal springs, may be used. Flexures 148 are two in number and extend from annular face 143 to directly engage or abut the underside of button face 128. During injection, when a user manually applies a plunging force onto proximal face 128, flexures 148 are elastically compressed until the small space previously existing between the distal face 131 of collar 130 and annular face 143 is closed, and the contacting distal face 131 and annular face 143 then serve together as a thrust bearing.

A hollow interior 149 of screw element 68 is defined by a cylindrical interior surface 150 provided with a helical threading 152 along its length. At least one tooth 154, such as two diametrically opposed teeth or a ring or teeth, is molded into screw element 68 at the intersection of annular face 143 and the interior surface 150. Teeth 154, when meshed with flange teeth 114, serve to rotatably lock together nut-engaging sleeve 110 and screw element 68, and thereby actuator 70 and screw element 68. Teeth 154 and 114 mesh when the flexures 148 have biased the screw element 68 and actuator 70 to the arrangement shown in FIGS. 2 and 3, and are not meshed or are disengaged when the flexures have been compressed during injecting to the arrangement shown in FIG. 4, which non-meshing permits relative rotation of screw element 68 and nut-engaging sleeve 110. In alternate embodiments, the actuator and screw element may be differently clutched together. For example, the nut-engaging sleeve may include one or more axially oriented teeth, such as a ring of four equally angularly spaced teeth, that extend in the proximal direction from face 116 and that are insertable into a circular array of holes in the screw element annular face 143. In such an alternate embodiment, one or more radially extending teeth, such as four equally angularly spaced teeth, similar to teeth 114 may still be provided to be engagable with drive sleeve teeth 164 described below to limit apparatus misuse.

Plunger or drive sleeve 66 is injection molded from plastic and includes a tubular body 160 that fits into the interior hollow 149 at a location radially outward of nut-engaging sleeve 110. Body 160 slides into and out from housing hollow 72 during pen use. A helical threading 162 is formed on the proximal region of body 160 along its exterior surface. Threading 162 engages the corresponding threading 152 formed on screw element 68 to threadedly engage the screw element 68 to the drive sleeve 66. Threadings 162 and 152 are shown as a double start threading but may be differently formed, such as a single start threading or another multiple start threading. The proximal end of body 160 is notched to form a ring of axially projecting teeth 164 that aid in limiting pen misuse as described below.

Drive sleeve 66 is keyed to the pen housing 60 to be rotatably fixed and axially moveable relative thereto. In the first embodiment, the keying is accomplished by at least one, such as a pair of diametrically opposed prongs 166 that axially extend from a flange 168 that radially projects from the distal end of body 160. Prongs 166 are sized and configured to be slidably received in a pair of diametrically arranged holes 79 provided in housing shoulder 77. In alternate embodiments, the keying of the housing and the drive sleeve can be differently provided, such as via radially extending prongs of the drive sleeve that slide within, for example, axially extending recesses or slots in the housing.

Still further, the keying can be accomplished via prongs of the housing that fit within openings in the drive sleeve, such as one or more prongs that axially project from shoulder 77 and fit through openings in flange 168 of drive sleeve 66.

The hollow interior of the drive sleeve body 160 includes a ring of axially extending, bi-directional ribs 170. An annular rib 172 extends transversely within the hollow at a location proximal of ribs 170. Rib 172 includes an angled distal face 174 that serves as an abutting surface for the nut 64, and further facilitates assembly by camming down the ramp-shaped proximal faces 104 of fingers 96 during assembly. Rib 172 axially fits in closely spaced relationship with rib faces 105 and rib face 95.

The threaded connections of the screw element and the housing, and the screw element and the drive sleeve, are non-binding to facilitate backdriving. Such connections are shown as formed by projecting, square-shaped threads that slide within corresponding designed recessed grooves or slots. It will be appreciated that the threading can be otherwise configured by the skilled artisan, such as the projecting threads and grooves being on opposite parts, or with different numbers of starts for the threadings, within the scope of the invention.

From the foregoing description, it will be recognized that as button 126 is manually turned during dose setting, the nut-engaging sleeve 110 rotatably fixed therewith also turns, and screw element 68 is caused to turn due to the clutched connection provided by the intermeshing teeth 114 and 154. Due to its threaded engagement with housing 60, screw element 68 screws out from the proximal end of the housing, bringing with it nut-engaging sleeve 110 and button 126 in this screwing motion. As screw element 68 screws out, drive sleeve 66, due to it being rotatably fixed relative to the housing and in a threaded connection with the screw element, is drawn by the screw element proximally and without rotation. The rotation of nut-engaging sleeve 110 during the dial screwing out causes a rotation of nut 64 proximally along the threading of the rotatably fixed drive screw 62.

The threading of screw element 68 to the housing 60, the drive sleeve 66 to the screw element 68, and the nut 64 to the drive screw 62, are designed together to obtain the mechanical advantage desired by the manufacturer, and further preferably are held within tolerances during manufacture such that during the dose setting described above, the drive sleeve 66 moves at the same speed and distance as nut 64 and neither promotes nor hinders the motion of nut 64 along the drive screw 62. In order to obtain a mechanical advantage of X between the motion of screw element 68 and drive screw 62 as set by the manufacturer, the threading of the screw element with the housing has a screw lead equal to X times the lead of the drive screw, and the threading of the screw element with the drive sleeve has a screw lead equal to (X−1) times the lead of the drive screw, wherein the lead refers to the axial distance traveled in a single revolution. A suitable mechanical advantage X for an insulin pen is believed to include 3 or 4, such as 3.4, and the screw lead of the drive screw 62 and nut 64 is selected by the manufacturer based upon how many revolutions or partial revolutions of the dial are desired in order to set an average dose. A suitable screw lead of the drive screw is about 0.1 inch, such as 0.108 inch. In addition, to ensure medication dose not drool from the device during dose setting, it is further preferred that the tolerances are held such that the screw lead of the drive screw, if not exactly equal to the screw lead of the threading of the screw element with the housing minus the screw lead of the threading of the screw element with the drive sleeve, is slightly less than such difference.

Referring now to FIGS. 7-18, one suitable sequence for assembling injection pen 20 is described. Such assembly may be performed manually, or alternatively in an automated fashion.

A first step of manufacturer assembly is to axially insert nut 64 into the drive sleeve 66 as shown in FIG. 7. The insertion proceeds as rib 172 engages fingers 96 and cams the fingers inward as the rib slides over proximal faces 104. When drive sleeve 66 reaches the point at which rib 172 fits between proximal face 95 and the distal faces 105, the resilient fingers 96 return outward to axially lock nut 64 relative to drive sleeve 66 in a rotatable fashion.

Figure 8:
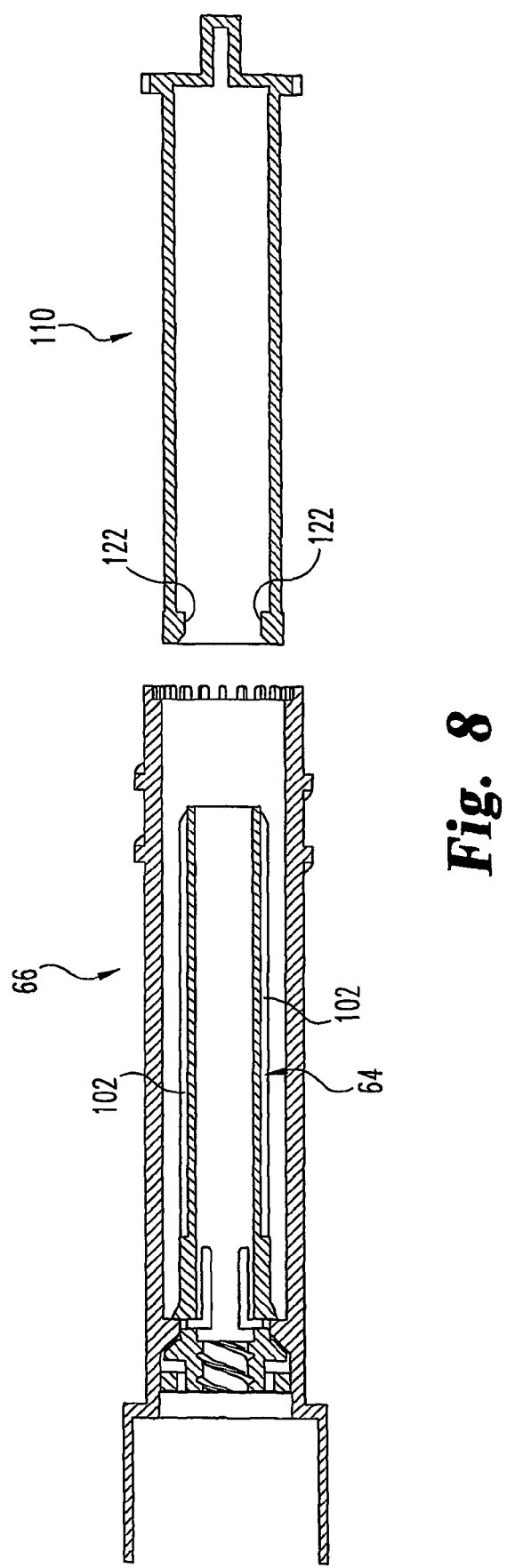
Figure 9:
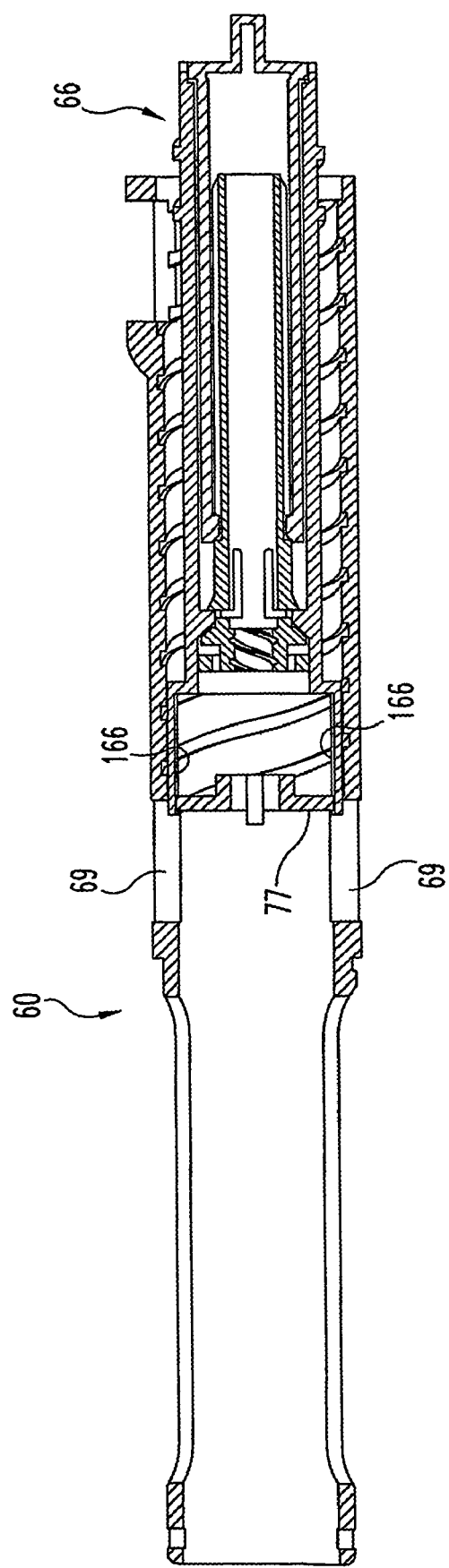

In the next assembly step, nut-engaging sleeve 110 is axially inserted as shown in FIG. 8, such that keys 122 are aligned with and slide into the longitudinal slots 102 of nut 64.

Next, the subassembly resulting from the FIG. 8 step is inserted into housing 60 such that prongs 166 of drive sleeve 66 insert through openings 79 in housing shoulder 77. A tool may be inserted radially inward through molding slots 69 formed in the housing body to hold the prongs inward for proper installation.

Figure 10:
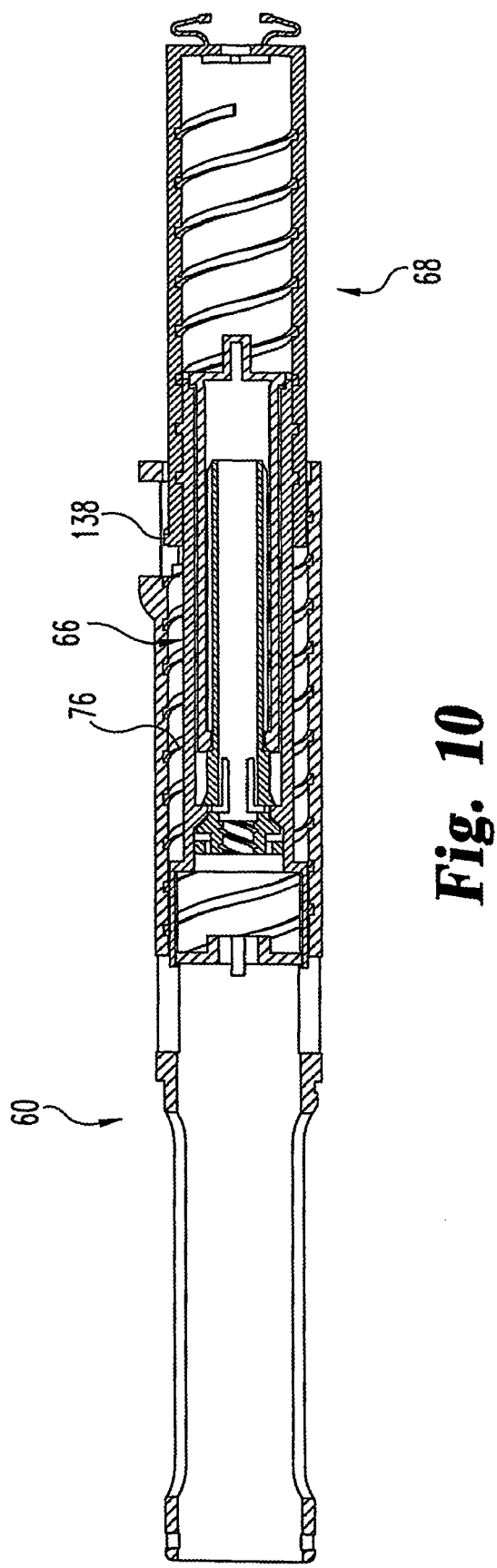
Figure 11:
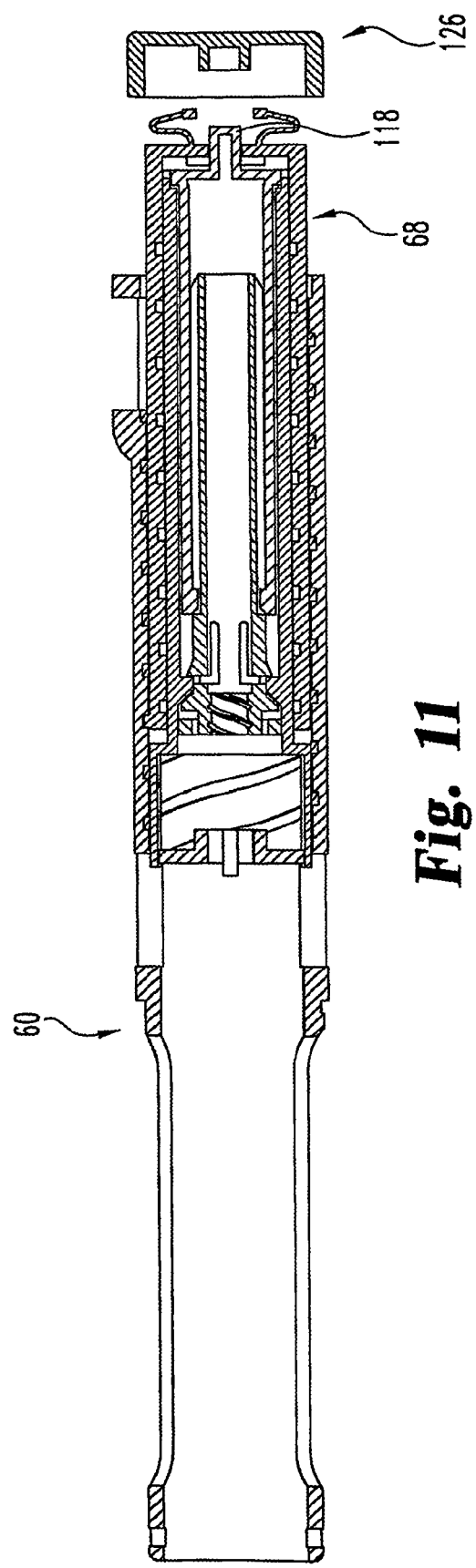

As shown in FIG. 10, screw element 68 is first screwed onto drive sleeve 66, and then screwed into the housing 60 such that threads 138 and 76 engage. As shown in FIG. 11, button 126 is then fixedly attached to the nut-engaging sleeve stem 118. It will be necessary to reach through the subassembly interior to support the nut-engaging sleeve for the joining operation.

Figure 12:
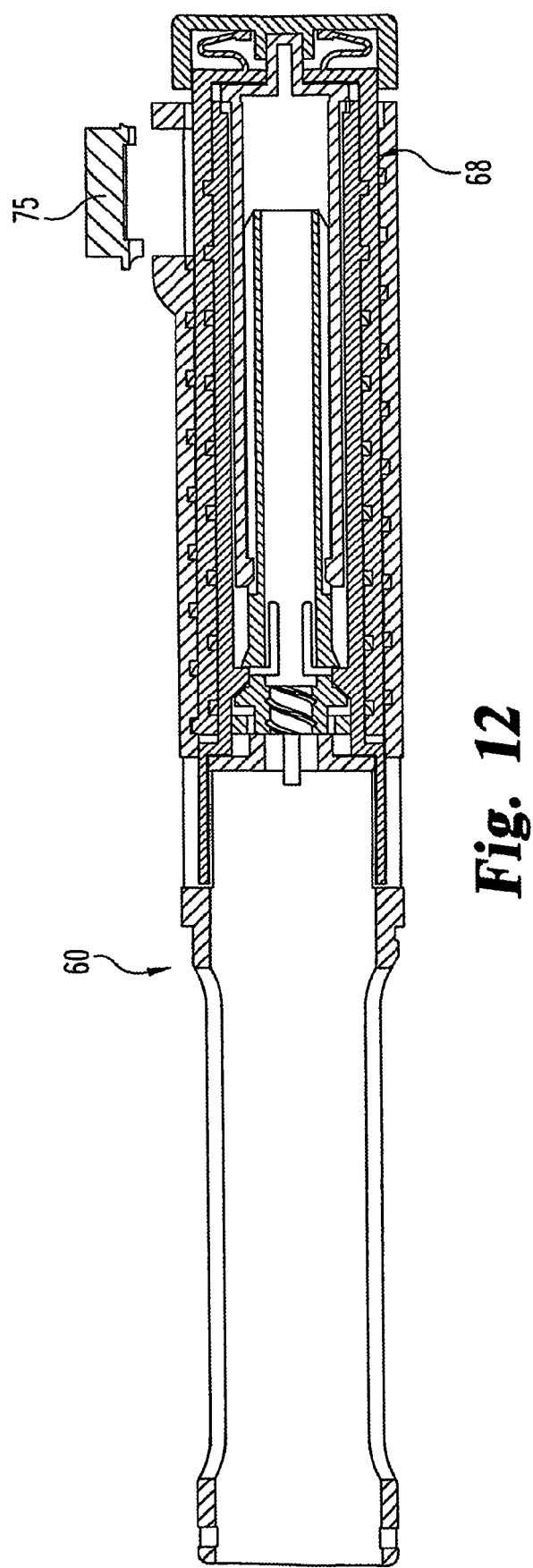
Figure 13:
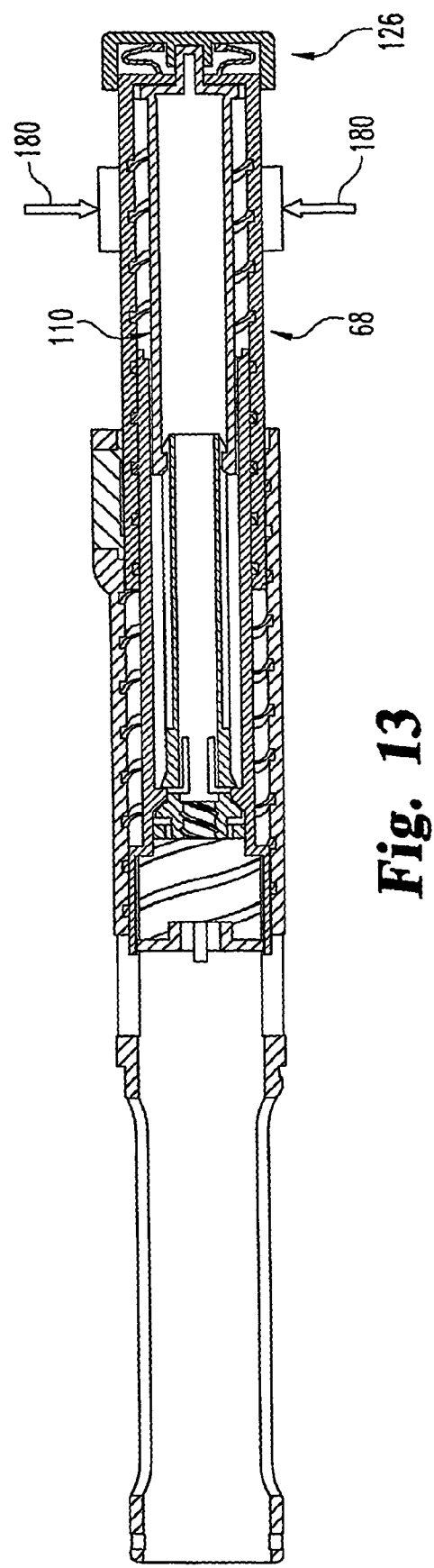

Lens 75 is then assembled to housing 60 as shown in FIG. 12. For the attachment features used in the first embodiment, the left-hand foot of the lens is first hooked into the housing body, and the right side is then snapped into place. When lens 75 is assembled to housing 60, the dial 68 is thereafter prevented from being completely screwed out and removed from the housing, as the underside of lens 75 is designed to form a stop for dial threads 138 at the maximum permitted dose of pen 20.

Button 126 is then rotated out, causing screw element 68 and nut-engaging sleeve 110 to rotate out. The screw element 68 is then clamped along its sides as abstractly represented at 180 in FIG. 13.

Figure 14:
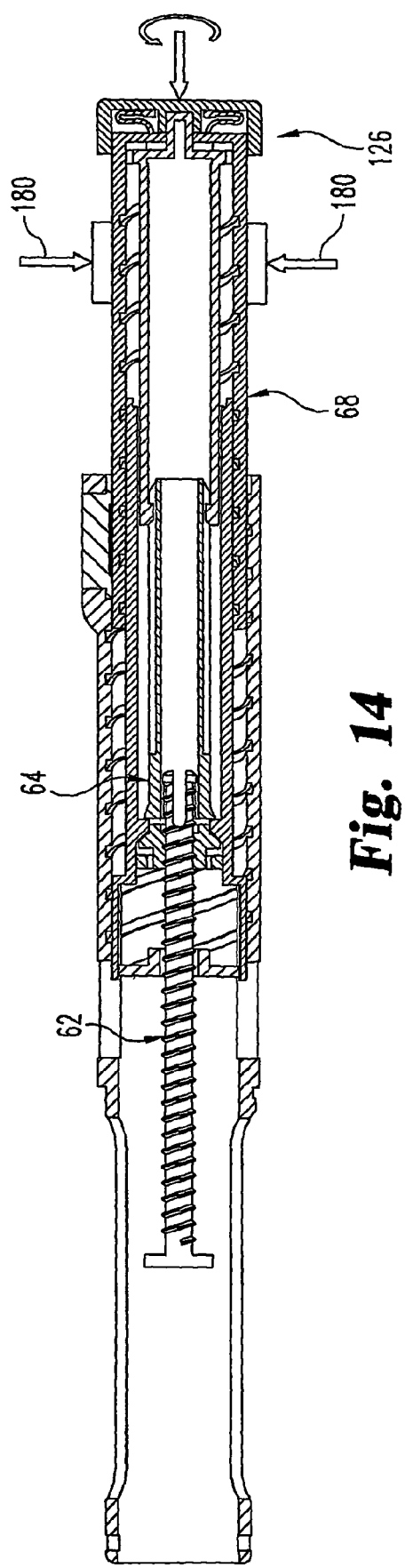

Next, while pressing button 126 to the left and rotating it in a counter-clockwise direction, as shown in FIG. 14, the drive screw 62 is axially inserted into nut 64, and the rotation of nut 64 pulls the screw proximally. Axial pressure on button 126 is then released, the clamping 180 is removed, and the button 126, screw element 68 and nut-engaging sleeve 110 are dialed back down as shown in FIG. 15 while the screw 62 remains in the same axial and rotational position.

Figure 15:
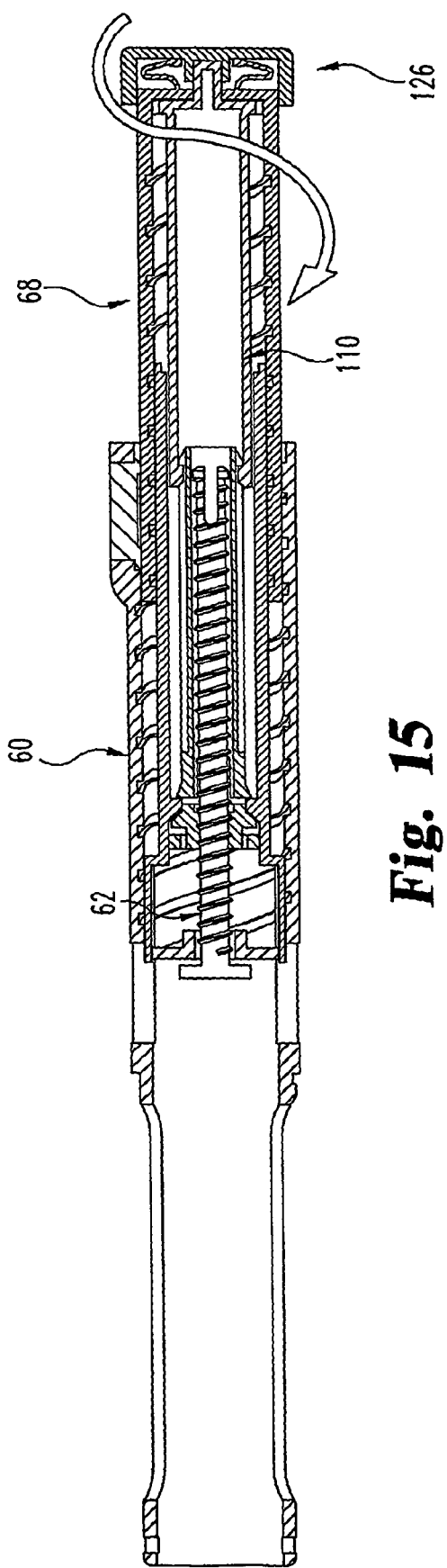
Figure 16:
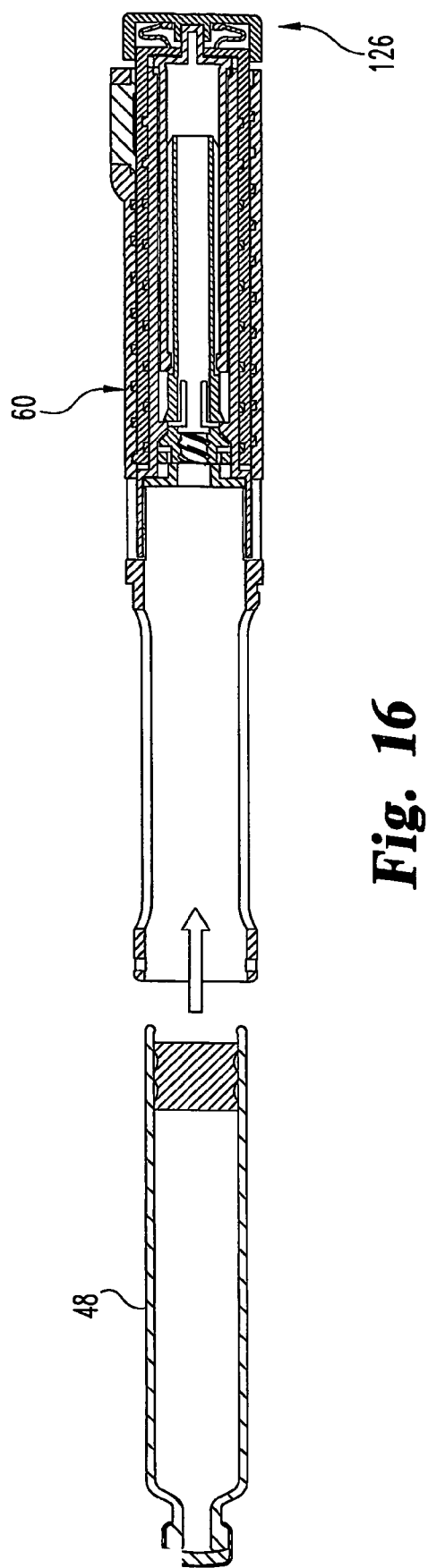
Figure 17:
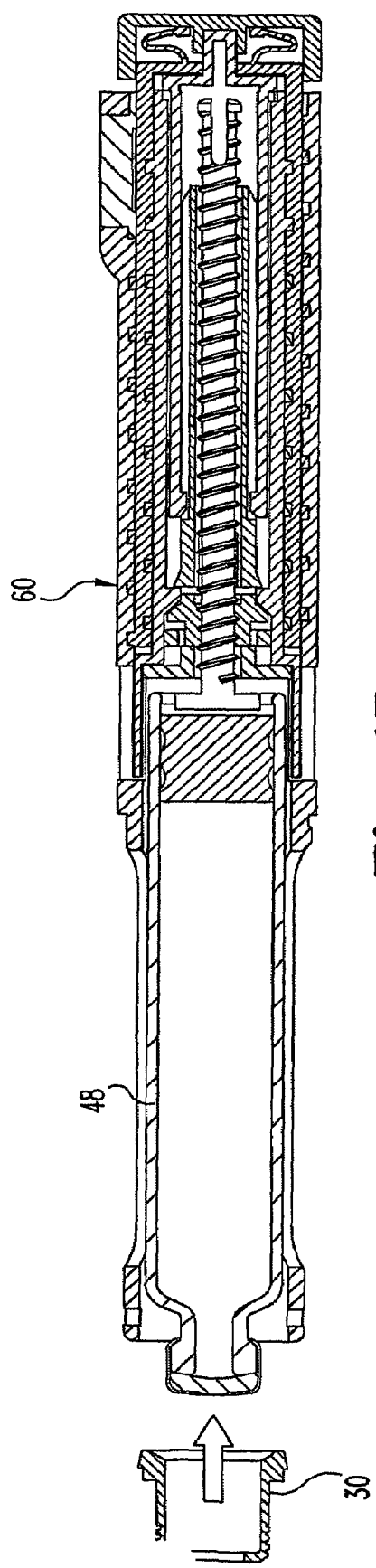

The subassembly of FIG. 15 then receives cartridge 48 as shown in FIG. 16, and then, as shown in FIG. 17, cap 30 is secured to the housing body 60 to capture cartridge 48 within the pen 20.

After the cartridge is secured, the manufacturer can preadjust pen 20 such that a known, for example two dose-unit gap exists between foot 90 of drive screw 62 and the cartridge piston 52, regardless of cartridge and pen component variability. This preadjustment simplifies a user's priming of the device for initial use. This preadjustment involves dialing out and clamping the screw element 68 as described with respect to FIG. 13 above, pressing and spinning button 126 in the clockwise direction and without axial motion of the screw element until a threshold torque is met that signals contact by screw foot 90 with cartridge piston 52, and then spinning the button back counterclockwise by a particular amount, such as, in the case of a two dose-unit rotation, approximately 36° in one embodiment. Next, the screw element 68 is released and the button 126 is allowed to automatically pop out under the influence of flexures 148. Button 126 and dial 68 are then screwed back down to a dose setting of zero, and the pen 20 is arranged as shown in FIGS. 1 and 2.

Figure 18:
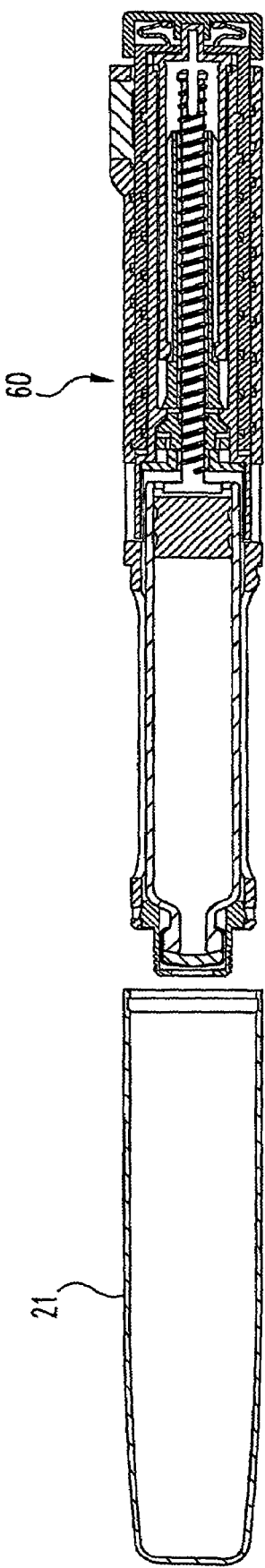

Cap 21 then can be axially aligned as shown in FIG. 18 and inserted onto the readied pen, and a label can be wrapped to the housing proximal portion.

The structure of injector pen 20 will be further understood in view of the following explanation of its operation. Initially, a user requiring a dose of medication will locate pen 20, which pen is typically in the ready or zero dose arrangement shown in FIG. 1, which is the arrangement in which the pen is provided to a user for its first use, or in which the pen remained after its previous use.

Pen 20 with a needle attached should first be primed, which priming step will be described but briefly as the internal workings of the pen during this operation will be appreciated from the further explanation below with respect to its injecting operation. In particular, typically while clutching the housing 60 in one hand, a user manually grips button flange 132 and then begins to turn button 126 relative to the housing 60. At the zero dose arrangement, and as long as button 126 is not also being plunged which is improper, button 126 can only be rotated in a dose increasing direction due to the dial not being further movable distally. At the zero dose arrangement, if a user attempts to push button 126 distally while turning it, which motion could affect the position of drive screw 62, such turning of the button is prevented by the meshing of nut-engaging sleeve teeth 114 with drive sleeve teeth 164. A user stops the rotating after a short amount of actuator travel that is associated with a small delivery volume, such as one or two units, which is indicated by the markings visible through lens 75. Then, and after removing cap 21 and any other needle cap present, and while pointing the needle tip 37 upward, the user applies a plunging force on button 126 to drive it distally until the screw element 68 returns to the zero dose position, at which the screw element threading 138 has reached the distal end of the housing threading 76, during which plunging action the piston 52 is shifted forward within cartridge 48. If a user sees that the piston movement has caused liquid to reach the needle distal tip 37, the priming process is complete. If no liquid is visible at needle tip 37, the priming steps are repeated as needed.

After priming, pen 20 is ready to be used for an actual injection. First, a user prepares the pen by setting the desired dose, as visible in lens 75, by turning of button 126. If the user dials up too large of a dose, and without expelling any medicine, the user can rotate down the dial by turning the button in the opposite direction, all the way back to zero if desired. After dose setting, the pen is generally arranged as shown in FIG. 3. To inject the dose, after pen 20 is manipulated so the injection needle distal tip 37 properly penetrates, for example, a user's skin, an axial, distal plunging force is applied to button face 128 to force actuator 70 distally toward the housing, such as with a thumb or index finger of the hand which grasps the housing. Initially during injecting, actuator 70 is shifted axially and without rotation relative to dial 68, which shifting motion compresses the biasing springs 148 to close the gap between button surface 131 and drive sleeve surface 143. The biasing springs are designed to compress prior to the dial 68 moving relative to the housing 60. When actuator 70 shifts relative to the dial 68 to the axial arrangement of the nut-engaging sleeve and dial shown in FIG. 4, the clutch teeth 114 and 154 disengage to allow a backdriving rotation of the dial relative to the actuator. During the axial movement of actuator 70 relative to dial 68, nut 64 does not move axially or rotationally. When the dial rotatably uncouples from the actuator 70, as the actuator is continued to be axially plunged without rotation by the user by the plunging of button 126, the dial 68 screws into the housing 60 as it spins relative to button 126 and the dose markings on the dial that indicate the amount still remaining to be injected is visible through lens 75. As it screws down, dial 68 causes drive sleeve 66 to in essence screw up the dial 68 threading as the drive sleeve advances distally a lesser distance than the dial. The advancement of drive sleeve 66, due to the abutting or direct engagement of rib 172 with the nut rib face 95, advances nut 64 without rotation, which due to its threaded connection with the screw advances the screw axially without rotation, which screw advancement shifts cartridge piston 52 to expel medication from the cartridge reservoir. The injection is completed when the screw element threading 138 has reached the distal end of the housing threading 76, at which time pen 20 is once again arranged in the ready state or zero dose position shown in FIGS. 1 and 2.

Pen 20 can continue to be used to deliver any desired dose until the medicine remaining in the cartridge is insufficient for a proper dosing. This insufficiency is indicated to a user by her inability to fully set the desired dose due to nut threading 100 abutting thread stop 86 of drive member 62, at which time the nut and actuator can not be rotated proximally any farther. When insufficient medicine remains, pen 20 is to be disposed of and replaced with a similar but entirely new pen.

Figure 19:
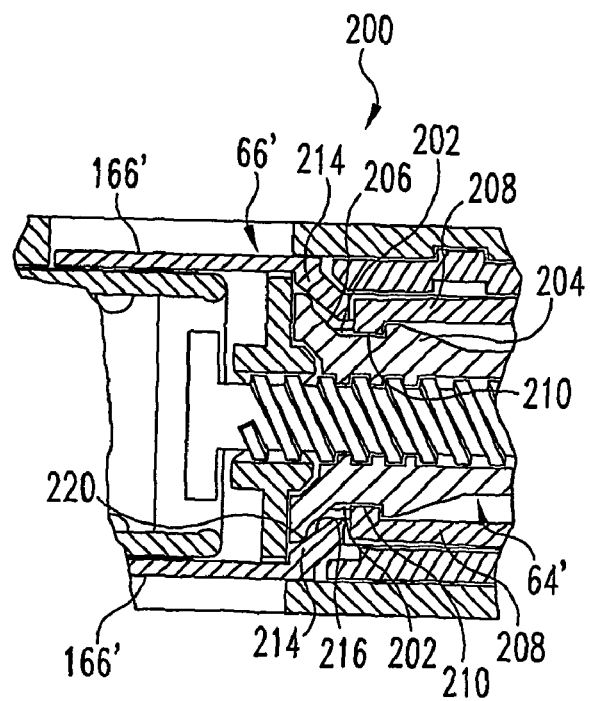
FIG. 19 is a partial front view in longitudinal cross-section of another medication dispensing apparatus of the present invention.

Referring now to FIG. 19, there is shown portions of another injector pen of the present invention, which pen is generally designated 200. Other than differences that are described below, pen 200 is identical to pen 20, and corresponding parts are identified with a prime reference. Pen 200 is designed differently from pen 20 to provide a nut and plunger engaging surface with a larger diameter, which can be used to better resist the nut from rotationally slipping relative to the plunger during injecting.

Nut 64' includes two sets of longitudinally extending ribs 202 that radially project from the nut body. The two sets of ribs each span 90° of the body circumference and are centered 180° apart, resulting in the nut body including around its entire circumference a series of four 90° segments alternately provided with and without ribs. Ribs 202 are axially disposed between a ramped shaped annular rib 204 and angled annular flange 206. Drive sleeve 66' is integrally formed with four axially-extending, resilient fingers 208 each with its own toothed bead 210. Fingers 208 with heads 210 are centered at 90° intervals around the drive sleeve circumference. All of heads 210 of fingers 208 snap over rib 204 during assembly, and facing pairs of beads 210, at different times of nut rotation, snap over ribs 202 to provide a dose-identifying clicking function during relative rotation of nut 64' and drive sleeve 66'. This finger and rib design facilitates molding while providing a suitable balancing of forces on the nut. If in an alternate embodiment the ribs were to extend continuously around the nut circumference, only two fingers centered 180° apart may be employed while still providing suitable force balancing. A flange 214 extending between the drive sleeve body and the locking prongs 166' has an angled or frustroconical interior surface 216. Flange surface 216 is adapted to frictionally engage the circumferential lock surface 220 of nut 64' during injecting. Interior surface 216 and lock surface 220 may have the shown cross-sectional shape around their entire peripheries. During injecting, as drive sleeve 66' is advanced distally to thereby simultaneously advance nut 64', the nut and drive sleeve are suitably rotatably fixed together by the frictional locking of the contacting conical surfaces.

Figure 20:
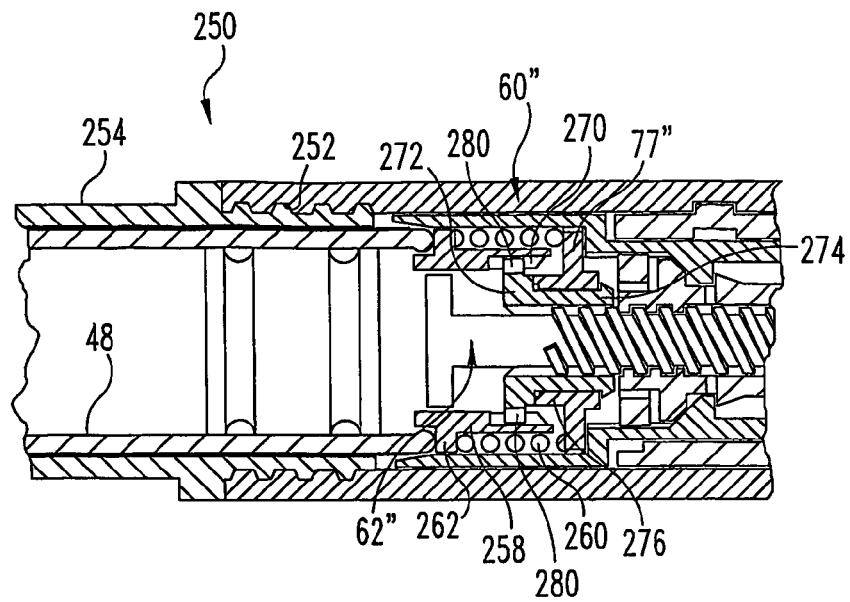
FIG. 20 is a partial front view in longitudinal cross-section of still another medication dispensing apparatus of the present invention.
Figure 21:
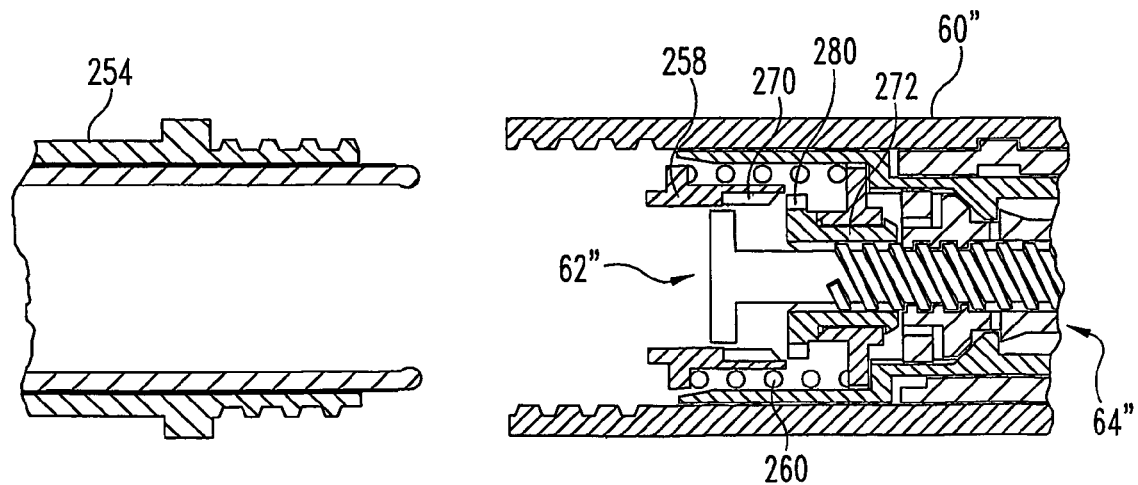
FIG. 21 is a partial front view in longitudinal cross-section conceptually similar to the view of FIG. 20, but after the dismounting of the cartridge retainer from the housing.
Figure 22:
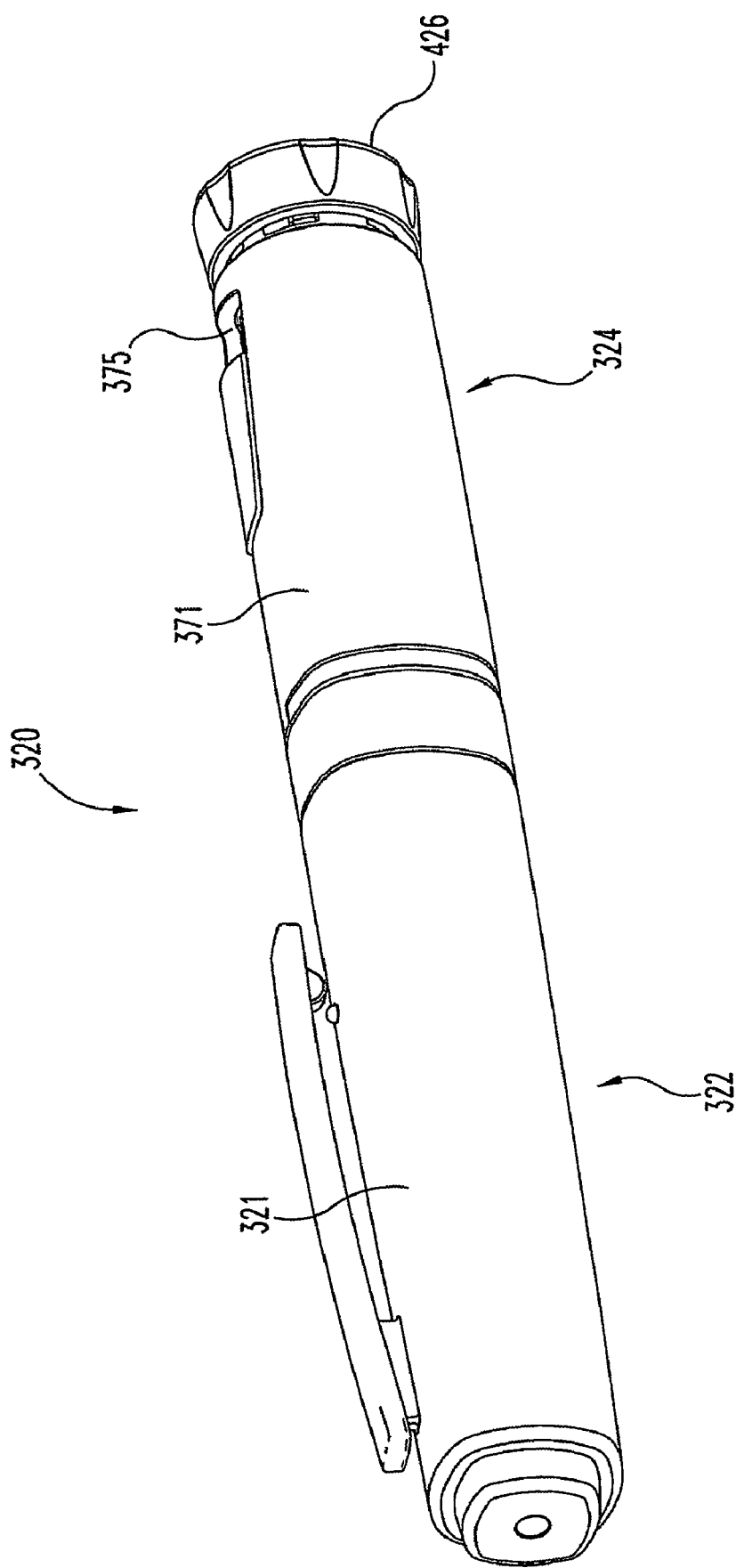
FIG. 22 is a front perspective view of another embodiment of a medication dispensing apparatus with mechanical advantage of the present invention, which apparatus is capped as well as arranged in a ready or zero dose state.
Figure 23:
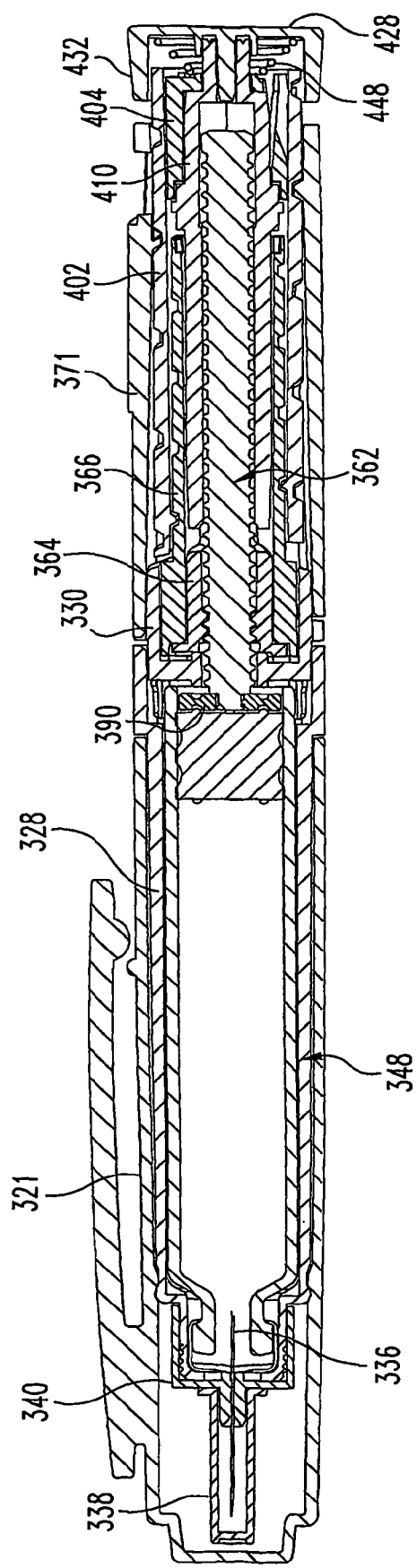
FIG. 23 is a front view in longitudinal cross-section of the medication dispensing apparatus of FIG. 22, wherein a capped needle assembly is shown provided.
Figure 24:
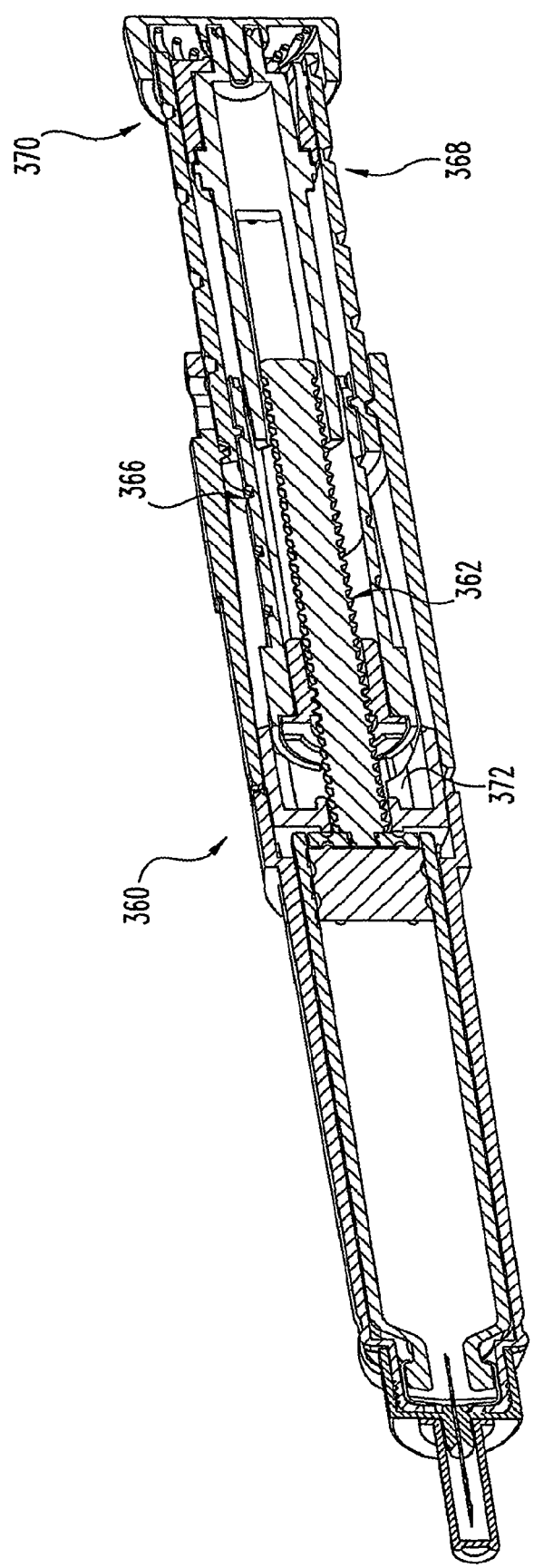
FIG. 24 is a front perspective view in longitudinal cross-section of the medication dispensing apparatus of FIG. 23, but with the apparatus cap removed, and after the apparatus has been manipulated from its ready state to a ready-to-inject state in which a maximum dose is to be dispensed.
Figure 25:
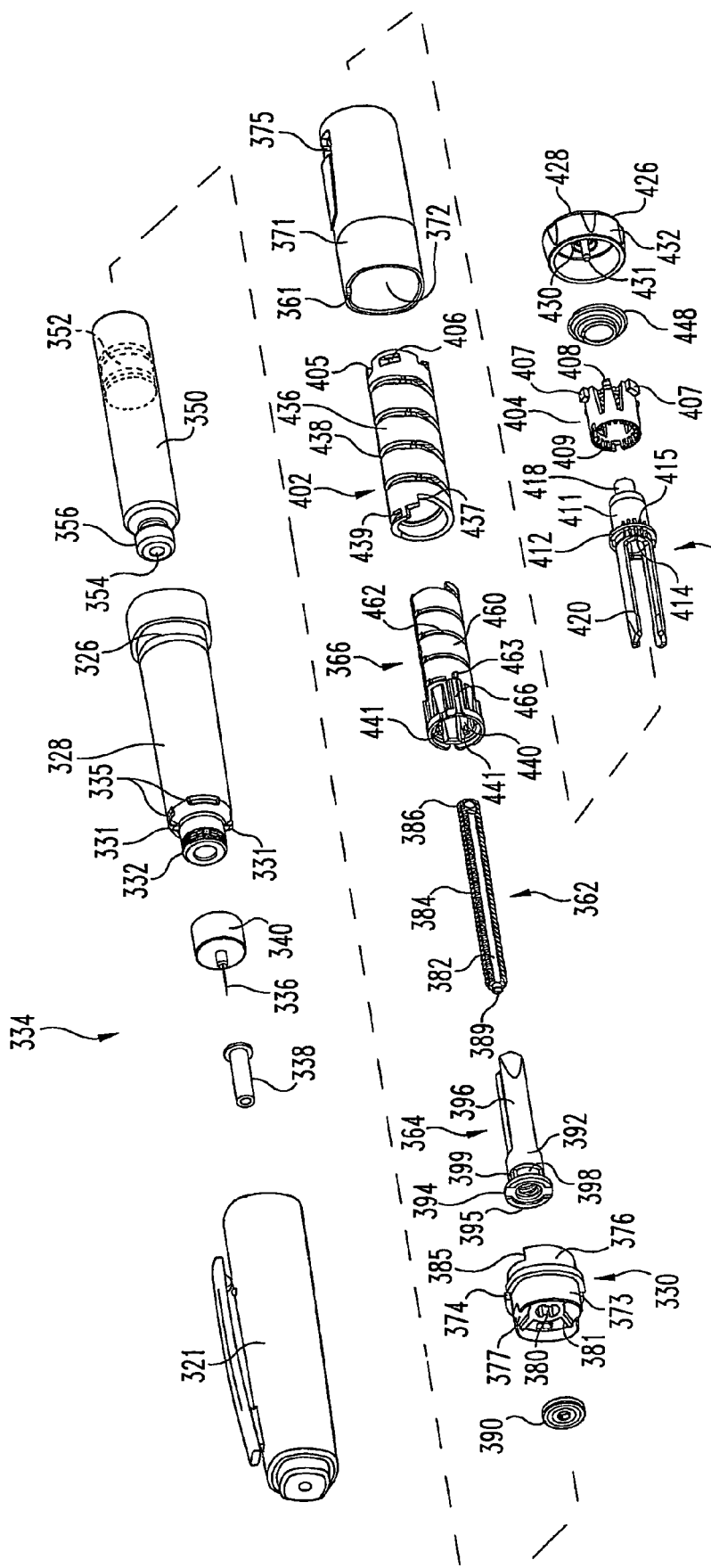
FIG. 25 is an exploded, perspective view of the apparatus of FIG. 23.
Figure 26:
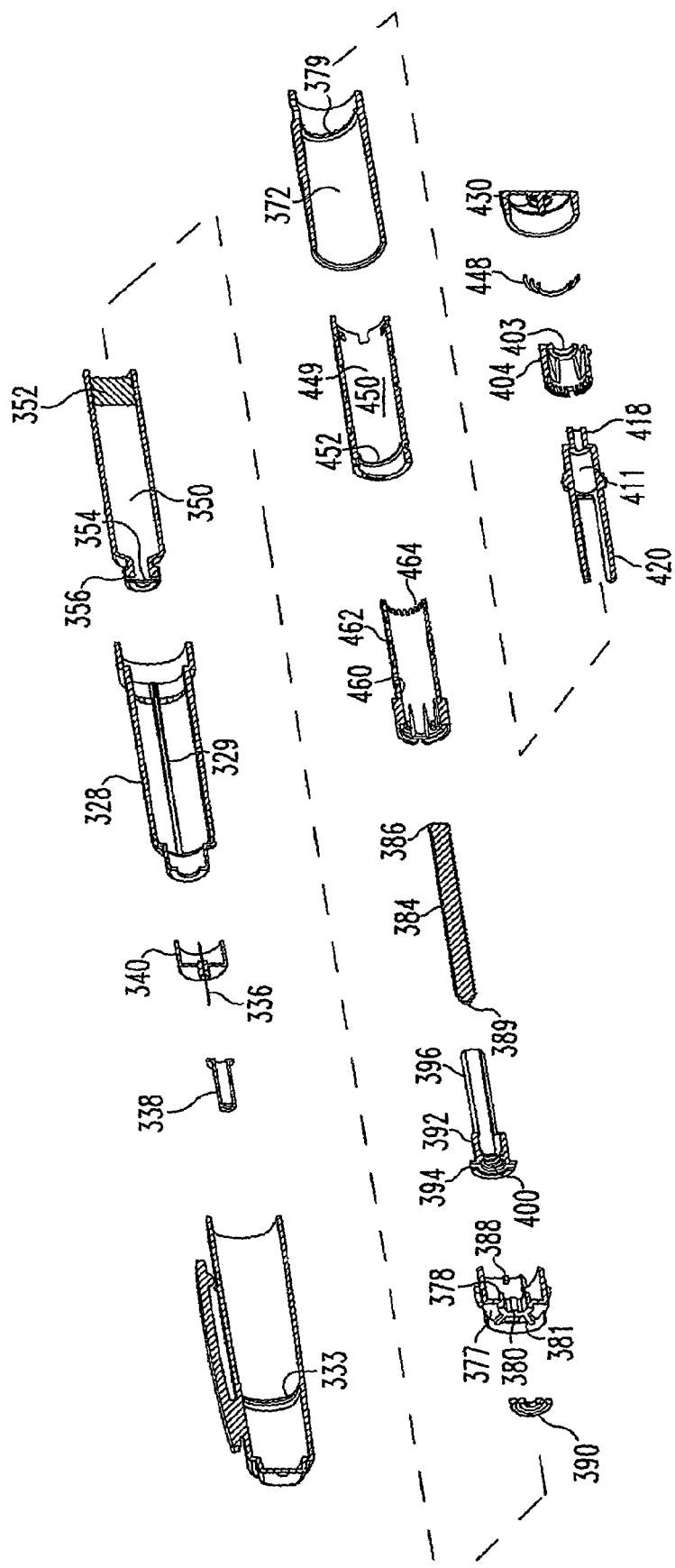
FIG. 26 is a longitudinal cross-sectional view of the apparatus of FIG. 25.

Referring now to FIGS. 20 and 21, there is shown portions of another injector pen of the present invention, which pen is generally designated 250. Pen 250 is conceptually similar in many respects to pen 20 of FIGS. 1-18, and corresponding parts are identified with a double prime reference, but pen 250 is adapted for use as a reusable device in which the held medicine cartridge can be removed when spent and replaced with a new cartridge.

In pen 250, the housing generally referenced at 60" is internally threaded at 252 and is adapted to threadedly receive the reusable cartridge holder or retainer 254 in which medication cartridge 48 is removably mounted. A tubular cartridge seat 258 rotationally keyed to housing 60" in a not shown fashion is biased distally by a spring 260 that abuts an annular face of seat shoulder 262 and the distal face of housing shoulder 77". The interior surface of seat 258 includes a ring of inwardly facing ribs or keys 270.

A tubular lock sleeve 272 includes prongs 274 to snap fit to a housing collar 276 to allow sleeve 272 to be rotatably free and axially fixed relative to housing 60". Lock sleeve 272 includes a pair of not shown, diametrically opposed, inwardly extending tabs that insert within the longitudinal grooves of drive screw 62" to allow drive screw 62" to be rotatably fixed and axially free relative to lock sleeve 272. Lock sleeve 272 includes at least one, such as a plurality of, radially outwardly facing teeth 280 that are complimentarily designed to cartridge seat ribs 270 to rotatably lock together lock sleeve 272 and seat 258 when engaged.

When a cartridge is installed as shown in FIG. 20, cartridge seat 258 is forced to its retracted or proximal position at which ribs 270 mesh with teeth 280. The resulting rotational locking of lock sleeve 272 to the rotationally locked seat 258 results in screw 62" being rotatably fixed within the housing, and reusable pen 250 can be operated similar to pen 20. When the cartridge is spent and retainer 254 is removed as shown in FIG. 21 to install a replacement cartridge, cartridge seat 258 travels to the extended position shown in FIG. 21, at which position it is axially retained within the housing in any suitable fashion, and at which lock sleeve teeth 280 are released and clear of ribs 270. As such, lock sleeve 272 is free to rotate with the drive screw 62" and relative to the housing 60" as the drive screw is pressed back, and thereby screwed into the axially stationary nut 64", to its starting position for use with the next cartridge. Drive screw 62" is shown in FIG. 21 after having been so pushed back. Although shown as having a one-piece construction, the drive screw 62" may be provided with a rotatably floating foot at its distal end to promote its back drive-ability.

In a not shown embodiment, the present invention may include an end of injection indicator that provides notice to the user that the pen is in the ready or zero dose position. One such indicator may include a resilient arm with a toothed end which projects from the proximal face of a shoulder or bulkhead similar to shoulder 77 of pen 20. The shoulder may be formed separate from but suitably attachable to the housing, and the arm with tooth may be integrally formed with such shoulder. The annular, distal face of the screw element or dial includes a detent which the clicker arm tooth snaps over when the screw element has been fully screwed distally or backdriven into the housing during injecting, which snapping motion provides a tactile and audible notice that the injection process has been completed, but which detent and tooth engagement does not prevent the screw element from being rotated out during dose preparing. To properly positively stop the distal travel of the screw element, and as is conveniently possible with a separately formed shoulder, a hard distal stop to prevent further dial screwing may be formed by the shoulder to be abutted by the screw element external threading at the zero dose position. For a pen with such a shoulder, and although an assembly sequence different than shown with respect to pen 20 would be required, the housing body could be molded such that the proximal end of screw element travel can be halted by a thread stop within the housing body which is abutted by the screw element external threading, and no lens, if not otherwise necessary for magnification or other purposes, would be required as the screw element disassembly function served by the lens of pen 20 is not needed.

In another not shown embodiment, the present invention may be modified to move threading 162 distally on the plunger body from the proximal region shown, which movement allows the axial length of threading 152 of screw element 68 to not extend as far proximally. Still further, such a design allows the plunger 66 to be shorter, as the plunger body proximally of the moved threads may be eliminated. To limit pen misuse, teeth 164 would be included on the new proximal end of the plunger body, and one or more radially extending teeth, such as four equally angularly spaced teeth, similar to teeth 114 would be moved distally on the nut-engaging sleeve to be properly engagable with the drive sleeve teeth 164.

Referring now to FIGS. 22-26, there is shown still another embodiment of a medication dispensing apparatus of the present invention. The apparatus, generally designated 320, is functionally similar to pen 20, and embodies a currently preferred overall configuration. Medication injector pen 320 is a prefilled, variable dose pen, suitable for delivery of any of a variety of therapeutics, such as insulin. Injector pen 320 generally includes a distal portion 322, which is received within pen cap 321 in FIGS. 22 and 23, and a proximal portion 324.

Distal portion 322 includes a retainer with a cartridge 348 held therein. The cartridge retainer is provided in the form of a tubular barrel 328 made of transparent plastic. Internal, longitudinally extending ribs 329 support the cartridge. An orienting skirt 326 of the barrel 328 is shaped to engage and automatically properly rotationally orient cap 321 when the cap is slid onto the cartridge retainer. Two snaps 331 on barrel 328 fit over a circumferential detent 333 formed in the interior of cap 321 to allow a releasable attachment of cap 321. As cap 321 is somewhat squarish in cross-section, the four slots 335 in barrel 328 provide clearance for the cap detent 333 when the cap is snapped on. The proximal end of barrel 328 is fixedly secured during pen assembly, such as with adhesives, to a mounting flange 373 of bulkhead portion 330 of the pen housing. Connection means, such as external threads 332, are provided on a stepped-down distal end of barrel 328 to releasably connect a known pen-needle assembly 334 that includes injection needle 336, hub 340 and needle cap 338. Cartridge 348 is of conventional design and includes reservoir 350, piston 352, septum 354 and cap 356.

Pen proximal portion 324 includes an external, protective housing 360, an axially advanceable drive member 362, a nut 364, a nut advancing plunger 366, a screw element 368, and an actuator 370 that is used to set the dose and then inject the set dose.

Housing 360 is formed from injection molded plastic bulkhead portion 330 and tubular body portion 371. A mounting flange 376 of bulkhead portion 330 inserts within and is fixedly secured, such as with adhesives, to body portion 371 during manufacturing assembly. Two diametrically opposed cutaways 385 are included in flange 376 to provide clearance for the distal end of screw element 368. Only one of cutaways 385 is actually used but two are provided to lessen the need for rotational orientation during assembly. Bulkhead portion 330 and body portion 371 are also keyed together via tab 361 and a slot 374 in a circumferential ridge around the bulkhead, which keying further ensures that the fixed connection of the housing pieces prevents relative rotation. The bulkhead ridge is shown with two such slots 374 spaced 180° apart to facilitate assembly.

Body portion 371 defines an internal hollow 372 in which drive member 362 extends in an axial direction. Housing window 375 allows dosage indicating markings on a dial portion within the housing to be readily visible during use.

Housing bulkhead portion 330 is formed with an inner annular shoulder 377 having a central opening ringed by boss 378. A pair of diametrically opposed tabs 380 extend inward from shoulder 377 into hollow 372. Tabs 380 slidably fit within longitudinal keyways 382 in drive member 362 to prevent drive member 362 from rotating within housing 360 during pen use, but permit drive member 362 to be shifted longitudinally. An opening-ringing boss with four equally angularly spaced, radially extending legs 381 distally project from shoulder 377, and the legs serve as abutments for the installed cartridge. Two diametrically opposed lugs 388 are formed on the interior surface of mounting flange 376 in axially spaced relationship with shoulder 377.

Drive member 362 is in the form of a screw that is axially translatable and rotatably fixed during dosing and injecting. Drive member 362 includes a shaft with a helical threading 384 along its length, which threading is interrupted by the longitudinally extending keyways or grooves 382. A thread stop 386 at the proximal end of threading 384 prevents the pen from being set by a user to deliver a dose of medicine larger than remains in cartridge 348. Drive member 362 engages the cartridge piston via an enlarged, disc-shaped foot 390 that snap fits to a mushroom-shaped head 389 formed at the end of drive member 362 so foot 390 is axially fixed to the drive member. Foot 390 is rotatable for the head shown, but need not be so to function appropriately for this embodiment.

Nut 364 is made from injection molded plastic and includes a cylindrical, tube-shaped body 392, plunging rib 394 and a pair of torque fingers 396. The distal region of body 392 is formed with an internal threading 400 that threadedly engages the drive screw threading 384 in a friction locking, or non-back-drivable, fashion. Threadings 400 and 384 are shown as a double start threading. Rib 394 radially protrudes from and extends circumferentially around body 392, the proximal face of which rib is directly engaged via abutting contact with plunger 366 during injecting. The distal face of rib 394 abuts bulkhead boss 378 when the nut is fully advanced to halt drive member movement, and thereby screw element movement, during an injection. Strengthening ribs 395 project from the distal face of rib 378, but have a larger inside diameter than the outside diameter of boss 378.

A circumferential recess 398 in the radial periphery of body 392 includes a series of axially extending ribs 399 that cooperate with complimentary elements provided on drive sleeve 366 to provide a clicker function during dose setting in either dose increasing or dose decreasing directions. In the shown embodiment, ribs 399 are provided in two 90° angular segments spaced by 90° ribless segments so as to cooperate with the four equally angularly spaced finger members provided on the drive sleeve. Torque fingers 396 are cooperatively designed with actuator 370 so that the actuator is axially free and rotatably fixed relative thereto.

In the shown embodiment, actuator 370 includes a nut-engaging sleeve 410 formed in one piece of an injection molded plastic and which fits within housing hollow 372. A flange 412 that rings a central region of the body 411 of sleeve 410 includes splines or teeth 414 that extend from the distal face of flange 412, and teeth 415 that extend from the proximal face of flange 412. A stepped-down portion of body 411 forms an axially extending stem 418. The distal end of body 411 includes a pair of fingers 420 that interfit with torque fingers 396 as to allow axial motion but not rotational motion of the nut 364 relative to the sleeve 410, thereby rotationally locking the pieces together within the same annular space. Fingers 396 and 420 extend sufficiently axially to ensure they do not disengage during the preparing of the maximum pen dose for injection. While fingers 396 and 420 are shown as pairs arranged diametrically, with each finger spanning 90°, different numbers and shapes of interfitting elements may be used within the scope of the invention.

Actuator 370 also includes an injection molded plastic button 426 with proximal face 428, and a distally facing and centrally located bearing collar 430 and alignment post 431. Stem 418 receives post 431 and is ultrasonically welded within collar 430 during manufacturing assembly, so as to axially and rotatably fix together button 426 and nut-engaging sleeve 410. Button lip 432 distally extends from the radial periphery of the button distal face to serve as a grip portion.

Coaxially mounted around nut-engaging sleeve 410 is screw element 368. Screw element 368 is formed in two injection molded plastic pieces by a main portion 402 and a flange 404. The cylindrical exterior surface 436 of screw element main portion 402 has a threading 438 formed as a helical groove that engages a corresponding threading 379 formed on the interior surface of housing body portion 371 to threadedly engage the screw element to the pen housing. Threadings 438 and 379 are shown as a single start threading but may be differently formed. Threading 379 abuts the end 439 of threading 438 at the maximum pen dose, assuming the cartridge is sufficiently full for such a maximum dose. A stop surface 437 of main portion 402 is positioned in slightly spaced apart relationship with a projecting stop 463 at the zero dose position, and stop surface 437 is to be abutted by stop 463 if a user attempts to manually screw the screw element below a zero dose position. Exterior surface 436 is sized to freely insert within button 426 such that depending lip 432 is disposed radially outward of and axially extends distally of the proximal end of screw element main portion 402.

A hollow interior 449 of screw element main portion 402 is defined by a cylindrical interior surface 450 provided with a helical threading 452. Threading 452 is shown as an inwardly projecting thread that spans about 350° of the interior. The proximal end region of main portion 402 includes three notches 405 and three windows 406 that are alternately spaced around the circumference. Screw element main portion 402 includes around its exterior surface 436 suitable indicia of therapeutic dose size as visible through housing opening 375.

The tubular flange 404 fits within the open proximal end of main portion 402. Ears 407 fit within notches 405 and assembly fingers 408 snap lock into windows 406 to axially and rotatably lock the screw element components 402 and 404 together during manufacturing assembly. A ring of axially extending teeth 409 formed in the interior surface of flange 404 cooperate with actuator teeth 415.

Disposed between the screw element 368 and actuator 370 is a tapered metal spring 448 that urges those components away from each other in an axial direction. A larger diameter end of spring 448 directly engages the underside of button face 428, and the smaller diameter, opposite end of spring 448 directly engages an apertured end face 403 of flange 404. During injection, when a user manually applies a plunging force onto proximal face 428, spring 448 is elastically compressed until bearing collar 430 contacts flange face 403 to serve as a thrust bearing. Flange teeth 409 and teeth 415 mesh when spring 448 has biased the screw element 368 and actuator 370 to the arrangement shown in FIG. 23, and are not meshed when the spring has been sufficiently compressed during injecting. While a tapered, helically coiled metal wire spring is shown, other forms of commonly known biasing elements may be substituted.

Plunger or drive sleeve 366 is injection molded from plastic and includes a tubular body 460 that fits into screw element hollow 449, and a helical threading 462 that engages screw element threading 452. Threadings 462 and 452 are shown as a single start threading, but may be differently formed. The proximal most portion of the end of body 460, which end is partially helically shaped corresponding to the threading, is notched to form a partial ring of axially projecting teeth 464 that, when meshed with actuator teeth 414, serve to rotatably lock together actuator 370 and plunger 366.

Drive sleeve 366 is keyed to pen housing 360 via a pair of ridge-defined slots 466 on the periphery of sleeve 366 which axially, slidably receive the lugs 388 radially inwardly projecting from housing bulkhead 330. Openings molded into drive sleeve 366 define four resilient fingers 440 having radially inwardly projecting teeth 441 that are axially oriented and shaped to project into recess 398 and click over, in either rotational direction, ribs 399 during dose setting. Fingers 440 with teeth 441 cooperate with recess 398 to hinder nut 364 from coming off plunger 366 after being assembled thereto during manufacture.

To facilitate back-driving in the embodiment of FIGS. 22-26, the threaded connections of the screw element and the housing, and the screw element and the drive sleeve, are non-binding and provided by projecting, 60° face angle threads that slide within correspondingly designed recessed grooves. With these threadings, it is preferred that the mechanical advantage is 3.4 or greater, and the screw lead of the drive member is 0.108 inch.

While this invention has been shown and described as having various designs, the present invention may be modified within the spirit and scope of this disclosure. For example, to deliver a fixed dose, the pen would preferably be modified such that the maximum that the dial could be screwed out to prepare the pen for injection would correspond to the fixed dose. Such a fixed dose pen could eliminate numerical dosage indicating marking, and instead provide user cues in the form of, for example, instructions and a graphical dosing indicator. This application is therefore intended to cover any variations, uses or adaptations of the invention using its general principles. Further, this application is intended to cover such departures from the present disclosure as come within known or customary practice in the art to which this invention pertains.

We claim:

1. A medication dispensing apparatus comprising:
   a housing;
   a drive member rotatably fixed during dose preparing and injecting and axially movable in a distal direction relative to said housing, said drive member including a threaded shaft;
   a fluid container defining a medicine-filled reservoir with a movable piston at one end and an outlet at the other end, said piston engagable by said drive member to be advanced toward said outlet when said drive member is moved distally;
   a nut screwable along said drive member threaded shaft;
   a screw element threadedly engaged with said housing to be screwable relative to said housing;
   a nut rotating element connected with said nut to be axially movable and rotatably fixed relative thereto, said nut rotating element rotatably fixed with said screw element when said nut rotating element and said screw element are in a first axial arrangement, said nut rotating element rotatable relative to said screw element when said nut rotating element and said screw element are in a second axial arrangement;
   a nut advancing plunger threadedly engaged with said screw element, said plunger axially movable and rotatably fixed relative to said housing;
   wherein the threading of said screw element to said housing is of a first lead, the threading of said plunger to said screw element is of a second lead, and the threading of said drive member threaded shaft is of a third lead, and said first lead, said second lead and said third lead are each a different value;
   wherein during dose preparing, said nut rotating element and said screw element are in said first axial arrangement, whereby a screwing motion of said nut rotating element and screw element relative to said housing screws said nut rotating element and said screw element a first axial distance from a home position, which screwing motion of said nut rotating element screws said nut along said drive member threaded shaft a second axial distance different than said first axial distance; and
   wherein during dose dispensing, said nut rotating element and said screw element are in said second axial arrangement, whereby a screwing motion of said screw element relative to said housing back toward said home position advances said plunger in said distal direction to axially advance said nut and thereby said drive member and said fluid container piston to dispense medicine from said outlet.

2. The medication dispensing apparatus of claim 1 wherein said nut rotating element comprises a sleeve portion within said screw element and a manually engageable button portion external to said screw element, said sleeve portion and button portion axially and rotatably shiftable as a unit.

3. The medication dispensing apparatus of claim 2 wherein said button portion is manually plunged during dose dispensing.

4. The medication dispensing apparatus of claim 3 wherein said button portion is manually rotated during dose preparing.

5. The medication dispensing apparatus of claim 2 wherein said button portion comprises a depending lip positioned radially outward of and axially extending distally of a proximal end of said screw element.

6. The medication dispensing apparatus of claim 2 further comprising means for biasing said nut rotating element and said screw element from said second axial arrangement toward said first axial arrangement.

7. The medication dispensing apparatus of claim 6 wherein said screw element and said nut rotating element comprise interfitting teeth that disengage when said biasing means are overcome to shift said nut rotating element and screw element from said first axial arrangement to said second axial arrangement.

8. The medication dispensing apparatus of claim 6 wherein said screw element comprises said biasing means that directly engage an underside of said button portion to force said button proximally relative to said screw element.

9. The medication dispensing apparatus of claim 1 wherein said screw element comprises a tubular member having a radially inner surface and a radially outer surface, wherein said outer surface is threaded to said housing, and wherein said inner surface is threaded to said plunger.

10. The medication dispensing apparatus of claim 1 wherein said nut comprises an extension having an axially extending keyway in an external surface, and wherein said nut rotating element comprises a key that slides within said keyway.

11. The medication dispensing apparatus of claim 1 wherein said nut and said nut rotating element comprise interfitting fingers that share an annular space.

12. The medication dispensing apparatus of claim 1 wherein said nut and said nut advancing plunger comprise cooperating clicker elements for creating audible indications during dose preparing.

13. The medication dispensing apparatus of claim 1 wherein said first lead equals a factor M times the third lead, and wherein said second lead equals a factor (M−1) times the third lead.

14. The medication dispensing apparatus of claim 1 wherein said nut advancing plunger is axially movable and rotatably fixed relative to said housing by at least one prong of said plunger that slidably fits within at least one opening formed in said housing.

15. The medication dispensing apparatus of claim 1 wherein said housing comprises a tubular body portion and a bulkhead portion that are adhesively fixedly secured together, said bulkhead portion including tabs that slidably fit within keyways in said drive member to prevent rotation of said drive member within said housing, wherein said nut advancing plunger is axially movable and rotatably fixed relative to said housing bulkhead portion by at least one lug of said housing bulkhead portion that slidably fits within at least one slot formed in said plunger.

16. The medication dispensing apparatus of claim 1 wherein said nut advancing plunger includes at least one flange that directly frictionally engages at least one flange of said nut during dose dispensing to resist nut rotation.

17. The medication dispensing apparatus of claim 9 wherein said screw element serves as a dial and comprises dose indication markings on said radially outer surface.

18. The medication dispensing apparatus of claim 1 wherein insulin is the medicine within the reservoir.

19. The medication dispensing apparatus of claim 1 further comprising a plurality of teeth on said nut advancing plunger that are engageable with at least one tooth on a portion of said nut rotating element to limit apparatus misuse.

20. The medication dispensing apparatus of claim 1 further comprising clicking means for identifying a dose setting, said clicking means including two sets of longitudinally extending ribs radially projecting from said nut, each set spanning 90° of the nut circumference and centered 180° apart from the other set, said clicking means further including four axially-extending, resilient toothed fingers of said plunger, said toothed fingers centered at 90° intervals around the circumference of said plunger.

21. The medication dispensing apparatus of claim 1 further comprising means for indicating an end of injection, said indicating means including a resilient arm with a toothed end which projects from and is integrally formed with a proximal face of a bulkhead separately formed and rotatably fixed to said housing, said indicating means further including a detent on an annular, distal face of said screw element which said toothed end of said arm snaps over when said screw element is frilly screwed distally into said housing during injecting, and wherein a portion of said bulkhead is abutted by and thereby forms a hard stop for said screw element when said screw element is fully screwed distally into said housing.

22. A medication dispensing apparatus comprising:
 a housing;
 a drive member rotatably fixed during dose preparing and injecting and axially movable in a distal direction relative to said housing, said drive member including a threaded shaft;
 a fluid container defining a medicine-filled reservoir with a movable piston at one end and an outlet at the other end, said piston engagable by said drive member to be advanced toward said outlet when said drive member is moved distally;
 a nut screwable along said drive member threaded shaft;
 a screw element threadedly engaged with said housing to be screwable relative to said housing;
 a nut rotating element connected with said nut to be axially movable and rotatably fixed relative thereto, said nut rotating element rotatably fixed with said screw element when said nut rotating element and said screw element are in a first axial arrangement, said nut rotating element rotatable relative to said screw element when said nut rotating element and said screw element are in a second axial arrangement;
 a nut advancing plunger threadedly engaged with said screw element, said plunger axially movable and rotatably fixed relative to said housing;
 wherein the threading of said screw element to said housing is of a first lead, the threading of said plunger to said screw element is of a second lead, and the threading of said drive member threaded shaft is of a third lead, wherein said first lead equals a factor M times the third lead, and wherein said second lead equals a factor (M−1) times the third lead;
 wherein during dose preparing, said nut rotating element and said screw element are in said first axial arrangement, whereby a screwing motion of said nut rotating element and screw element relative to said housing screws said nut rotating element and said screw element a first axial distance from a home position, which screwing motion of said nut rotating element screws said nut along said drive member threaded shaft a second axial distance different than said first axial distance; and
 wherein during dose dispensing, said nut rotating element and said screw element are in said second axial arrangement, whereby a screwing motion of said screw element relative to said housing back toward said home position advances said plunger in said distal direction to axially advance said nut and thereby said drive member and said fluid container piston to dispense medicine from said outlet.

\* \* \* \* \*

UNITED STATES PATENT AND TRADEMARK OFFICE
CERTIFICATE OF CORRECTION

PATENT NO.         : 7,291,132 B2
APPLICATION NO. : 10/567196
DATED              : November 6, 2007
INVENTOR(S)        : Otto Daniel DeRuntz It is certified that error appears in the above-identified patent and that said Letters Patent is hereby corrected as shown below:

<u>On Title page should read,</u>

Insert Item -- [60]      Related U.S. Application Data

Provisional application No. 60/494,499, filed on August 12, 2003. --

Signed and Sealed this

Eighth Day of July, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,291,132 B2 | Page 1 of 1 |
| APPLICATION NO. | : 10/567196 | |
| DATED | : November 6, 2007 | |
| INVENTOR(S) | : Otto Daniel DeRuntz | |

It is certified that error appears in the above-identified patent and that said Letters Patent is hereby corrected as shown below:

On the first page of the specification, insert the following cross-reference after the title:

-- This is the national phase application, under 35 USC 371, for PCT/US2004/022312, filed 09 August 2004, which claims the benefit, under 35 USC 119(e), of US provisional application 60/494,499 filed 12 August 2003. --

Signed and Sealed this

Thirtieth Day of September, 2008

JON W. DUDAS
*Director of the United States Patent and Trademark Office*